(12) United States Patent
Huang et al.

(10) Patent No.: US 7,314,716 B2
(45) Date of Patent: Jan. 1, 2008

(54) GUSTDUCIN γ SUBUNIT MATERIALS AND METHODS

(75) Inventors: Liquan Huang, Havertown, PA (US); Robert F. Margolskee, Upper Montclair, NJ (US); Marianna Max, Montclair, NJ (US); Y. Gopi Shanker, Waltham, MA (US)

(73) Assignee: Mount Sinai School of Medicine, New York, NY (US)

( * ) Notice: Subject to any disclaimer, the term of this patent is extended or adjusted under 35 U.S.C. 154(b) by 700 days.

(21) Appl. No.: 10/161,941

(22) Filed: Jun. 3, 2002

(65) Prior Publication Data

US 2003/0166103 A1    Sep. 4, 2003

Related U.S. Application Data

(63) Continuation of application No. 09/443,958, filed on Nov. 19, 1999, now abandoned.

(51) Int. Cl.
  *G01N 33/53* (2006.01)
  *C07K 14/00* (2006.01)
  *C01N 15/00* (2006.01)
  *C01N 7/01* (2006.01)

(52) U.S. Cl. .................. 435/7; 530/350; 536/23.1; 435/320.1; 435/235.1; 435/69.1

(58) Field of Classification Search ............... None
  See application file for complete search history.

(56) References Cited

U.S. PATENT DOCUMENTS

| | | |
|---|---|---|
| 3,647,482 A | 3/1972 | Yueh |
| 3,784,390 A | 1/1974 | Hijiya et al. |
| 4,243,691 A | 1/1981 | Mohlenkamp, Jr. et al. |
| 4,544,559 A | 10/1985 | Gil et al. |
| 4,562,020 A | 12/1985 | Hijiya et al. |
| 4,623,394 A | 11/1986 | Nakamura et al. |
| 4,826,824 A | 5/1989 | Schiffman |
| 4,994,442 A | 2/1991 | Gil et al. |
| 5,232,735 A | 8/1993 | Kurtz et al. |
| 5,411,945 A | 5/1995 | Ozaki et al. |
| 5,518,902 A | 5/1996 | Ozaki et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,637,618 A | 6/1997 | Kurtz et al. |
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,654,311 A | 8/1997 | Kurtz et al. |
| 5,665,755 A | 9/1997 | Kurtz et al. |
| 5,688,662 A | 11/1997 | Margolskee |
| 5,693,756 A | 12/1997 | Li et al. |
| 5,700,792 A | 12/1997 | Kurtz et al. |
| 5,703,053 A | 12/1997 | Kurtz et al. |
| 5,817,759 A | 10/1998 | Margolskee |
| 5,853,792 A | 12/1998 | Zolotov et al. |
| 5,866,608 A | 2/1999 | Kurtz et al. |
| 6,008,250 A | 12/1999 | Kurtz et al. |
| 6,015,792 A | 1/2000 | Kurtz et al. |
| 2001/0022964 A1 | 9/2001 | Leung et al. |
| 2003/0157568 A1 | 8/2003 | Zuker et al. |

FOREIGN PATENT DOCUMENTS

| | | |
|---|---|---|
| CH | 497 136 | 11/1970 |
| EP | 0 059 363 B1 | 12/1984 |
| EP | 0 122 400 B1 | 7/1987 |
| EP | 0 125 021 B1 | 9/1993 |
| EP | 0 416 667 B1 | 9/1993 |
| JP | 45-51605 | 6/1970 |
| JP | 48-17044 B4 | 3/1973 |
| JP | 48-10227 B4 | 4/1973 |
| JP | 61-271969 A2 | 12/1986 |
| JP | 1285157 | 11/1989 |

(Continued)

OTHER PUBLICATIONS

Ming et al, Proc Natl. Acad. Sci. USA, vol. 95, 8933-8938, Jul. 1998.*
Ueda et al, J. Biol Chem., vol. 369, 4388-4395, Feb. 1994.*
Ruiz-Avila et al , Proc Natl. Acad. Sci. USA, vol. 98, 8868-8873, Jul. 2001.*
He et al Chem. Senses, vol. 27, 719-727, 2002.*
Huang et al Nature Neuroscience, vol. 2, No. 12, 1055-1062, Dec. 1999.*
Lindorfer et al ,J. Biol Chem., vol. 273, No. 51, 34429-34436, Dec. 1998.*

(Continued)

*Primary Examiner*—Christine J. Saoud
*Assistant Examiner*—Nirmal S Basi
(74) *Attorney, Agent, or Firm*—Nixon Peabody LLP

(57) ABSTRACT

Gustducin is a taste receptor cell heterotrimeric guanine nucleotide binding protein. Disclosed herein is the amino acid sequence of the gamma (γ) subunit of gustducin, as well as polynucleotide sequences encoding the γ subunit. Also disclosed are methods of modifying taste involving agents that inhibit or activate the gustducin γ subunit, methods for identifying such taste modifying agents and various taste modifying agents.

10 Claims, 1 Drawing Sheet

FOREIGN PATENT DOCUMENTS

| | | |
|---|---|---|
| JP | 52-36885 | 9/1993 |
| JP | 10108655 | 4/1998 |
| JP | 11-169131 | 6/1999 |
| JP | 2000-300206 A | 10/2000 |
| JP | 2001-269149 A | 10/2001 |
| RU | 2003265 C1 | 11/1993 |
| WO | WO 91/09955 A1 | 7/1991 |
| WO | WO 92/20808 A1 | 11/1992 |
| WO | WO 94/12650 A2 | 6/1994 |
| WO | WO 97/04666 A1 | 2/1997 |
| WO | WO 98/20862 A1 | 5/1998 |
| WO | WO 98/26763 A1 | 6/1998 |
| WO | WO 98/26780 A2 | 6/1998 |
| WO | WO 99/17753 A1 | 4/1999 |
| WO | WO 00/038536 A2 | 7/2000 |

OTHER PUBLICATIONS

Rahmatullah et al, J. Biol Chem., vol. 270, 2946-2951, Feb. 1995.*

Blake et al, J. Biol Chem., vol. 276, 49267-49274, 2001.*

Cane et al., "Harnessing the Biosynthetic Code: Combinations, Permutations, and Mutations," *Science* 282(5386):63-68 (1998).

Capecchi, "Altering the Genome by Homologous Recombination," *Science* 244(4910):1288-1292 (1989).

Cheung et al., "Specific Activation of $G_s$ by Synthetic Peptides Corresponding to an Intracellular Loop of the β-Adrenergic Receptor," *FEBS Lett.* 279(2):277-280 (1991).

Duby et al., "Using Synthetic Nucleotides as Probes," in Current Protocols in Molecular Biology 6.4.1-6.4.10 (Ausubel et al. eds., Supp. 2 1988, Supp. 9 1990, Supp. 13 1995).

Houghten et al., "Generation and Use of Synthetic Peptide Combinatorial Libraries for Basic Research and Drug Discovery," *Nature* 354(6348):84-86 (1991).

Jones & Reed, "$G_{olf}$: An Olfactory Neuron Specific-G Protein involved in Odorant Signal Transduction," *Science* 244(4906):790-795 (1989).

Lam et al., "A New Type of Synthetic Peptide Library for Identifying Ligand-binding Activity," *Nature* 354(6348):82-84 (1991).

Lerea et al., "Identification of Specific Transducin α Subunits in Retinal Rod and Cone Photoreceptors," *Science* 234(4772):77-80 (1986).

Peri et al., "Rapid Entry of Bitter and Sweet Testants Into Liposomes and Taste Cells: Implications for Signal Transduction," *Am. J. Physiol. Cell Physiol.* 278:C17-C25 (2000).

Quertermous, "Plating Libraries and Transfer to Filter Membranes," in Current Protocols in Molecular Biology 6.1.1-6.1.4 (Ausubel et al. eds., Supp. 13 1995 & Supp. 34 1996).

Rahmatullah & Robishaw, "Direct Interaction of the α and γ Subunits of the G Proteins," *J. Biol. Chem.* 269(5):3574-3580 (1994).

Ruiz-Avila et al., "An In Vitro Assay Useful to Determine the Potency of Several Bitter Compounds," *Chem. Senses* 25:361-368 (2000).

Ruiz-Avila et al., "Coupling of Bitter Receptor to Phosphodiesterase Through Transducin in Taste Receptor Cells," *Nature* 376:80-85 (1995).

Sambrook et al., Molecular Cloning 9.47-9.51 (2d ed. 1989).

Schmidt et al., "Specificity of G Protein β and γ Subunit Interactions," *J. Biol. Chem.* 267(20)13807-13810 (1992).

Scott & Smith, "Searching for Peptide Ligands with an Epitope Library," *Science* 249(4967):386-390 (1990).

Strauss, "Hybridization with Radioactive Probes," in Current Protocols in Molecular Biology 6.3.1-6.3.6 (Ausubel et al. eds., 1987, Supp. 2 1988, Supp.13 1995, Supp. 24 1993).

Tareilus et al., "Approaches for Monitoring Rapid Kinetics of Second Messenger Signaling," in Current Techniques & Protocols 193-202 (1995).

Weis, "Planting and Transferring Cosmid and Plasmid Libraries," in Current Protocols in Molecular Biology 6.2.1-6.2.3 (Ausubel et al eds., 1987 & Supp. 24 1993).

Wong et al., "Biochemical and Transgenic Analysis of Gustducin's Role in Bitter and Sweet Transduction," in LXI Cold Spring Harbor Symposia on Quantitative Biology 173-184 (1996).

Akabas et al., "A Bitter Substance Induces a Rise in Intracellular Calcium in a Subpopulation of Rat Taste Cells," *Science* 242:1047-50 (1988).

Amer & Kreighbaum, "Cyclic Nucleotide Phosphodiesterases: Properties, Activators, Inhibitors, Structure-activity Relationships, and Possible Role in Drug Development," *J. Pharm. Sci.* 64(1):1-37 (1975).

Asano et al., "Reconstitution of Catecholamine-stimulated Binding of Guanosine 5'-O- (3-Thiotriphosphate) to the Stimulatory GTP-binding Protein of Adenylate Cyclase," *Biochem.* 23:5460-7 (1984).

Avenet & Lindemann, "Perspectives of Taste Reception," *J. Membr. Biol.* 112(1)1-8 (1989).

Avenet et al., "Transduction in Taste Receptor Cells Requires cAMP-dependent Protein Kinase," *Nature* 331:351-4 (1988).

Axelsson et al., "The Influence of Dietary Nucleotides on Erythrocyte Membrane Fatty Acids and Plasma Lipids in Preterm Infants," *Acta Paediatr.* 86(5):539-44 (1997).

Bartoshuk, "Taste Mixtures: Is Mixture Suppression Related To Compression?," *Physiol. Behav.* 14:643-9 (1975).

Béhé et al., "Membrane Currents in Taste Cells of the Rat Fungiform Papilla," *J. Gen. Physiol.* 96:1061-84 (1990).

Benedetti et al., "Sweet and Bitter Taste: Structure and Conformations of Two Aspartame Dipeptide Analogues," *J. Pept. Sci.* 1:349-59 (1995).

Bernhardt et al., "Changes in $IP_3$ and Cytosolic $Ca^{2+}$ in Response to Sugars and Non-sugar Sweeteners in Transduction of Sweet Taste in the Rat," *J. Physiol.* 490(2):325-36 (1996).

Birnbaumer, "G Proteins in Signal Transduction," *Ann. Rev. Pharmacol. Toxicol.* 30:675-705 (1990).

Birnbaumer et al., "Receptor-effector Coupling by G Proteins," *Biochim. Biophys. Acta* 1031:163-224 (1990).

Boughter, Jr. et al., "Differential Expression of α-Gustducin in Taste Bud Populations of the Rat and Hamster," *J. Neurosci.* 17(8):2852-58 (1997).

Bruch & Kalinoski, "Interaction of GTP-binding Regulatory Prteins with Chemosensory Receptors," *J. Biol. Chem.* 262(5):2401-4 (1987).

Bubis & Khorana, "Interaction in the Complex Between β- and γ-Subunits of Transducin," *J. Biol. Chem.* 265(22)12995-9 (1990).

Cagan & Morris, "Biochemical Studies of Taste Sensation: Binding to Taste Tissue of $^3$H-labeled Monellin, a Sweet-tasting Protein," *Proc. Nat'l Acad. Sci. USA* 76(4):1692-6 (1979).

Chaudhari & Roper, "Molecular and Physiological Evidence of Glutamate (Umami) Taste Transduction via a G Protein-coupled Receptor," *Ann. NY Acad. Sci.* 855:398-406 (1998).

Chaudhari et al., "The Taste of Monosodium Glutamate: Membrane Receptors in Taste Buds," *J. Neurosci.* 16(12):3817-26 (1996).

Cummings et al., "Sweet Taste Transduction in Hamster: Sweeteners and Cyclic Nucleotides Depolarize Taste Cells by Reducing a $K^+$ Current," *J. Neurophysiol.* 75(3):1256-63 (1996).

Drewnowski et al., "Taste Responses and Preferences for Sweet High-fat Foods: Evidence for Opioid Involvement," *Physiol. Behav.* 51:371-9 (1992).

Dum et al., "Activation of Hypothalamic β-Endorphin Pools by Reward Induced by Highly Palatable Food," *Pharmacol. Biochem. Behav.* 18:443-7 (1983).

Formaker & Frank, "Responses of the Hamster Chorda Tympani Nerve to Binary Component Taste Stimuli: Evidence for Peripheral Gustatory Mixture Interactions," *Brain Res.* 727:79-90 (1996).

Fung & Nash, "Characterization of Transducin from Bovine Retinal Rod Outer Segments," *J. Biol. Chem.* 258(17):10503-10 (1983).

Fung et al., "Flow of Information in the Light-triggered Cyclic Nucleotide Cascade of Vision," *Proc. Nat'l Acad. Sci. USA* 78(1):152-6 (1981).

Genbank Accession No. A1454466, Jul. 5, 1999.

Genbank Accession No. AL031033, Jun. 26, 2007.

Genbank Accession No. H46116, Jul. 31, 1995.

Gilbertson, "Gustatory Mechanisms for the Detection of Fat," *Curr. Opin. Neurobiol.* 8:447-52 (1998).

Gilberton et al., "Fatty Acid Modulation of K⁺ Channels in Taste Receptor Cells: Gustatory Cues for Dietary Fat," *Am. J. Physiol.* 272:C1203-C1210 (1997).

Gilbertson et al., "Proton Currents Through Amiloride-sensitive Na Channels in Hamster Taste Cells," *J. Gen. Physiol.* 100(5):803-24 (1992).

Gillespie, "Phosphodiesterases in Visual Transduction by Rods and Cones," in Cyclic Nucleotide Phosphodiesterases: Structure, Regulation and Drug Action 163-84 (Joe Beavo & Miles D. Houslay eds., 1990).

Glendinning, "Is the Bitter Rejection Response Always Adaptive?," *Physiol. Behav.* 56(6):1217-27 (1994).

Greenberg et al., "Stimulation of Neuronal Acetylcholine Receptors Induces Rapid Gene Transcription," *Science* 234:80-3 (1986).

Halliday et al., "Limited Trypsin Proteolysis of Photoreceptor GTP-binding Protein," *j. Biol. Chem.* 259(1):516-25 (1984).

Hamm et al., "Site of G Protein Binding to Rhodopsin Mapped with Synthetic Peptides from the α Subunit," *Science* 241(4867):832-5 (1988).

Harder et al., "Assessing Gustatory Detection Capabilities Using Preference Procedures," *Chem. Senses* 14(4):547-64 (1989).

Heck et al., "Salt Taste Transduction Occurs Through an Amiloride-sensitive Sodium Transport Pathway," *Science* 223:403-5 (1984).

Herness & Gilbertson, "Cellular Mechanisms of Taste Transduction," *Ann. Rev. Physiol.* 61:873-900 (1999).

Higginbotham et al., "Flavour Potentiating Properties of Talin Sweetener (Thaumatin)," in The Quality of Foods and Beverages 91-111 (George E. Inglett ed., 1981).

Hoon et al., "Functional Expression of the Taste Specific G-protein, α-Gustducin," *Biochem. J.* 309:629-36 (1995).

Hoon et al., "Putative Mammalian Taste Receptors: A Class of Taste-specific GPCRs with Distinct Topographic Selectivity," *Cell* 96:541-51 (1999).

Kakkar et al., "Calmodulin-dependent Cyclic Nucleotide Phosphodiesterase (PDE1)," *Cell Mol. Life Sci.* 55(8-9):1164-86 (1999).

Kinnamon, "Taste Transduction: A Diversity of Mechanisms," *Trends. Neurosci.* 11(11)491-6 (1988).

Kinnamon & Margolskee, "Mechanisms of Taste Transduction," *Curr. Opin. Neurobiol.* 6(4):506-13 (1996).

Kinnamon & Roper, "Membrane Properties of Isolated Mudpuppy Taste Cells," *J. Gen. Physiol.* 91:351-71 (1988).

Kinnamon et al., "Apical Localization of K³⁰ Channels in Taste Cells Provides the Basis for Sour Taste Transduction," *Proc. Nat'l Acad. Sci. USA* 85:7023-7 (1988).

Kolesnikov & Margolskee, "A Cyclic-nucleotide-suppressible Conductance Activated by Transducin in Taste Cells," *Nature* 376(6535):85-8 (1995).

Komuro & Rakic, "Orchestration of Neuronal Migration by Activity of Ion Channels, Neurotransmitter Receptors, and Intracellular $Ca^{2+}$ Fluctuations," *J. Neurobiol.* 37(1):110-30 (1998).

König et al., "Three Cytoplasmic Loops of Rhodopsin Interact with Transducin," *Proc. Nat'l Acad. Sci. USA* 86:6878-82 (1989).

Krieg & Melton, "In Vitro RNA Synthesis with SP6 RNA Polymerase," *Methods Enzymol.* 155:397-415(1987).

Kurihara & Koyama, "High Activity of Adenyl Cyclase in Olfactory and Gustatory Organs," *Biochem. Biophys. Res. Commun.* 48(1):30-4 (1972).

Laemmli, "Cleavage of Structural Proteins During the Assembly of the Head of Bacteriophage T4," *Nature* 227:680-5 (1970).

Lee, "The Chemistry and Biochemistry of the Sweetness of Sugars," in 45 Advances in Carbohydrate Chemistry and Biochemistry 199-351 (1987).

Lindemann, "Taste Reception," *Physiolog. Rev.* 76(3)719-66 (1996).

Lochrie et al., "Sequence of the Alpha Subunit of Photoreceptor G Protein: Homologies Between Transducin, ras, and Elongation Factors," *Science* 228:96-9 (1985).

Margolskee, "The Biochemistry and Molecular Biology of Taste Transduction," *Curr. Opin. Neurobiol.* 3(4):526-31 (1993).

Margolskee, "The Molecular Biology of Taste Transduction," *BioEssays* 15(10):645-50 (1993).

Mazzoni et al., "Structural Analysis of Rod GTP-binding Protein, $G_t$," *J. Biol. Chem.* 266(21):14072-81 (1991).

McLaughlin et al., Abstract 184, "Gustducin: A Tasteful G Protein," *Chem. Senses* 17(5):667 (1992).

McLaughlin et al., "Gustducin and Transducin: A Tale of Two G Proteins," *Ciba Found. Symp.* 179:186-96; discussion 196-200 (1993).

McLaughlin et al., "Gustducin Is a Taste-cell-specific G Protein Closely Related to the Transducins," *Nature* 357:563-9 (1992).

McLaughlin et al., "Molecular Cloning of G Proteins and Phosphodiesterases from Rat Taste Cells," *Physiol. Behav.* 56(6):1157-64 (1994).

Medynski et al., "Amino Acid Sequence of the α Subunit of Transducin Deduced from the cDNA Sequence," *Proc. Nat'l Acad. Sci. USA* 82(13):4311-5 (1985).

Ming et al., "Blocking Taste Receptor Activation of Gustducin Inhibits Gustatory Responses to Bitter Compounds," *Proc. Nat'l Acad. Sci. USA* 96:9903-8 (1999).

Mirenowicz & Schultz, "Preferential Activation of Midbrain Dopamine Neurons by Appetitive Rather than Aversive Stimuli," *Nature* 379:449-51 (1996).

Morton, "Sour Orange,"Fruits of Warm Climates 130-3 (1987) at http://www.hort.purdue.edu/newcrop/morton/sourorange.html (last accessed Jun. 21, 2007).

Naim et al., "Some Taste Substances Are Direct Activators of G-proteins," *Biochem. J.* 297:451-4 (1994).

Navon & Fung, "Characterization of Transducin from Bovine Retinal Rod Outer Segments," *J. Biol. Chem.* 263(1):489-96 (1988).

Neer et al., "Analysis of G-protein α and βγ Subunits by in Vitro Translation," *Methods Enzymol.* 237:226-39 (1994).

Ninomiya et al., "Gustatory Neural Responses in Three Different Strains of Mice," *Brain Res.* 302(2):305-14 (1984).

Ninomiya et al., "Lack of Guramarin Sensitivity of Sweet Taste Receptors Innervated by the Glossopharyngeal Nerve in C57BL Mice," *Am. J. Physiol.* 272(3 Pt 2):R1002-R1006 (1997).

Peterson, "A Simplification of the Protein Assay Method of Lowry et al. Which Is More Generally Applicable," *Anal. Biochem.* 83(2):346-56 (1977).

Price, "Phosphodiesterase in Tongue Epithelium: Activation by Bitter Taste Stimuli," *Nature* 241:54-5 (1973).

Raintree Nutrition Inc., "Database File for: Bitter Orange (*Citrus aurantium*)," *Tropical Plant Database*, http://www.rain-tree.com/orange.htm (1996) (last accessed Jun. 21, 2007).

Rarick et al., "A Site on Rod G Protein α Subunit That Mediates Effector Activation," *Science* 256:1031-3 (1992).

Rodbell et al., "The Glucagon-sensitive Adenyl Cyclase System in Plasma Membranes of Rat Liver. V. An Obligatory Role of Guanylnucleotides in Glucagon Action," *J. Biol. Chem.* 246(6):1877-82 (1971).

Roper, "The Cell Biology of Vertebrate Taste Receptors," *Ann. Rev. Neurosci.* 12:329-53 (1989).

Rosenzweig et al., "Possible Novel Mechanism for Bitter Taste Mediated Through cGMP," *J. Neurophysiol.* 81:1661-5 (1999).

Rössler et al., "Identification of a Phospholipase C β Subtype in Rat Taste Cells," *Eur. J. Cell Biol.* 77:253-61 (1998).

Roy, "A Review of Sweet Taste Potentiation Brought About by Divalent Oxygen and Sulfur Incorporation," *Crit. Rev. Food Sci. Nutr.* 31(1/2):59-77 (1992).

Schiffman & Gatlin, "Sweeteners: State of Knowledge Review," *Neurosci. Biobehav. Rev.* 17:313-45 (1993).

Schiffman et al., "Amiloride Reduces the taste Intensity of Na⁺ and Li⁺ Salts and Sweeteners," *Proc. Nat'l Acad. Sci. USA* 80:6136-40 (1983).

Seidman, "Screening of Recombinant DNA Libraries, " in Current Protocols in Molecular Biology 6.0.3-6.0.5 (Ausubel et al. eds., 1994).

Shimazaki et al., "Photoaffinity Labeling of Thaumatin-binding Protein in Monkey Circumvallate Papillae," *Biochim. Biophys. Acta* 884:291-8 (1986).

Shin et al., "Structure-Taste Correlations in Sweet Dihydrochalcone, Sweet Dihydroisocoumarin, and Bitter Flavone Compounds," *J. Med. Chem.* 38(21):4325-31 (1995).

Simon et al., "Diversity of G Proteins in Signal Transduction," *Science* 252:802-8 (1991).

Sonnenburg et al., "Identification, Quantitation, and Cellular Localization of PDE1 Calmodulin-stimulated Cyclic Nucleotide Phosphodiesterase," *Methods* 14(1):3-19 (1998).

Spielman, "Gustducin and Its Role in Taste," *J. Dent. Res.* 77(4):539-44 (1998).

Spielman et al., "A Rapid Method of Collecting Taste Tissue from Rats and Mice," *Chem. Senses* 14(6):841-6 (1989).

Spielman et al., "Generation of Inositol Phosphates in Bitter Taste Transduction," *Physiol. Behav.* 56(6)1149-55 (1994).

Spielman et al., "Rapid Kinetics of Second Messenger Production in Bitter Taste," *Am. J. Physiol.* 270:C926-C931 (1996).

Strathmann et al., "Diversity of the G-protein Family: Sequences from Five Additional α Subunits in the Mouse," *Proc. Nat'l Acad. Sci. USA* 86:7407-9 (1989).

Striem et al., "Sweet Tastants Stimulate Adenylate Cyclase Coupled to GTP-binding Protein in Rat Tongue Membranes," *Biochem. J.* 260:121-6 (1989).

Stryer & Bourne, "G Proteins: A Family of Signal Transducers," *Annu. Rev. Cell Biol.* 2:391-419 (1986).

Sugawara et al., "Profile of Nucleotides and Nucleosides of Human Milk," *J. Nutr. Sci. Vitaminol.* 41(4):409-18 (1995).

Takami et al., "Human Taste Cells Express the G Protein α-Gustducin and Neuron-specific Enolase," *Mol. Brain Res.* 22(1-4):193-203 (1994).

Tam, "Synthetic Peptide Vaccine Design: Synthesis and Properties of a High-density Multiple Antigenic Peptide System," *Proc. Nat'l Acad. Sci. USA* 85:5409-13 (1988).

Tanabe et al., "Primary Structure of the α-Subunit of Transducin and Its Relationship to ras Proteins," *Nature* 315(6016):242-5 (1985).

Thomas et al., "Identification of Synaptophysin as a Hexameric Channel Protein of the Synaptic Vesicle Membrane," *Science* 242(4881):1050-3 (1988).

Tonosaki & Funakoshi, "Cyclic Nucleotides May Mediate Taste Transduction," *Nature* 331:354-6 (1988).

Tsunenari et al., "Activation by Bitter Substances of a Cationic Channel in Membrane Patches Excised from the Bullfrog Taste Receptor Cell," *J. Physiol.* 519:397-404 (1999).

Weishaar et al., "A New Generation of Phosphodiesterase Inhibitors: Multiple Molecular Forms of Phosphodiesterase and the Potential for Drug Selectivity," *J. Med. Chem.* 28(5):537-45 (1985).

Wong et al., "Transduction of Bitter and Sweet Taste by Gustducin," *Nature* 381:796-800 (1996).

Yatsunami & Khorana, "GTPase of Bovine Rod Outer Segments: The Amino Acid Sequence of the α Subunit as Derived from the cDNA Sequence," *Proc. Nat'l Acad. Sci USA* 82:4316-20 (1985).

\* cited by examiner

```
mgust    MEEWDVPQMKKEVESLKYQLAFKREMSSKTIPELLKWIEDGIPKDPFLNPDLMKNNPWVEKAK-CTIL 67
hgust    MEEWDVPQMKKEVESLKYQLAFQREMASKTIPELLKWIEDGIPKDPFLNPDLMKNNPWVEKGK-CTIL 67
y8cone   MAQDLSEKDLLKMEVEQLKKEVKNTRIPISKAGKEIKEYVEAQAGNDPFLKGIPEDKNPFKEKGG-CLIS 69
y2       MASNNTASIAQARKLVEQLKMEANIDRIKVSKAAADLMAYCEAHAKEDPLLTPVPASENPFREKKFFCAIL 71
y4       MKEGMSNNSTTSISQARKAVEQLKMEACMDRVKVSQAASDLLAYCEAHVREDPLIIPVPASENPFREKKFFCTIL 75
y11      MPALHIEDLPEKEKLKMEVEQLRKEVKLQRQQVSKCSEEIKNYIEERSGEDPLVKGIPEDKNPFKEKGS-CVIS 73
y7       MSATNNIAQARKLVEQLRIEAGIERIKVSKASSELMSYCEQHARNDPLLVGVPASENPFKDKKP-CIIL 68
y8olf    MSNNMAKIAEARKTVEQLKLEVNIDRMKVSQAAAELLAFCETHAKDDPLVTPVPAAENPFRDKRLFCTLL 70
y3       MKGETPVNSTMSIGQARKMVEQLKIEASLCRIKVSKAAADLMTYCDAHACEDPLITPVPTSENPFREKKFFCALL 75
y1       MPVINIEDLTEKDKLKMEVDQLKKEVTLERMLVSKCCEEFRDYVEERSGEDPLVKGIPEDKNPFKELKGGCVIS 74
y5       MSGSSVAAMKKVVQQLRLEAGLNRVKVSQAAADLKQFCLQNAQHDPLLTGVSSSTNPFRPQKV-CSFL 68
y10      MSSGASASASALQRLVEQLKLEAGVERIKVSQAAAELQQYCMQNACKDALLVGVPAGSNPFREPRS-CALL 68
y12      MSSKTASTNNIAQARRTVQQLRMEASIERIKVSKASADLMSYCEEHARNDPLLMGIPTSENPFKDKKT-CTIL 72
```

FIGURE 1

SEQUENCE LISTING

```
<160> NUMBER OF SEQ ID NOS: 20

<210> SEQ ID NO 1
<211> LENGTH: 346
<212> TYPE: DNA
<213> ORGANISM: Mus musculus
<220> FEATURE:
<221> NAME/KEY: CDS
<222> LOCATION: (90)..(293)
<220> FEATURE:
<223> OTHER INFORMATION: gamma13 clone 1

<400> SEQUENCE: 1
gactccacag atccctcggc ccttgtcatc tctgcttttg ctgtctcctc caaaacctca      60
ggctggctac caccgacgcc cccgacgcc atg gag gag tgg gat gtg ccc cag     113
                                Met Glu Glu Trp Asp Val Pro Gln
                                  1               5 atg aag aag gag gta gag agc ctc aag tac caa ctg gcc ttc aag agg     161
Met Lys Lys Glu Val Glu Ser Leu Lys Tyr Gln Leu Ala Phe Lys Arg
     10                  15                  20
```

```
gag atg tcg tcc aag acc atc ccc gag ctt ctc aag tgg att gag gat     209
Glu Met Ser Ser Lys Thr Ile Pro Glu Leu Leu Lys Trp Ile Glu Asp
     25              30              35              40 gga atc ccc aag gac ccc ttc ctg aac cca gac ctg atg aag aac aac     257
Gly Ile Pro Lys Asp Pro Phe Leu Asn Pro Asp Leu Met Lys Asn Asn
             45              50              55 cct tgg gta gag aag gcc aag tgc acc atc cta tga gcctgaccca          303
Pro Trp Val Glu Lys Ala Lys Cys Thr Ile Leu
         60                  65 cactctctgt aaggtgtgac tttataaata gacttctccg ggt                     346

<210> SEQ ID NO 2
<211> LENGTH: 67
<212> TYPE: PRT
<213> ORGANISM: Mus musculus

<400> SEQUENCE: 2

Met Glu Glu Trp Asp Val Pro Gln Met Lys Lys Glu Val Glu Ser Leu
 1               5                  10                  15

Lys Tyr Gln Leu Ala Phe Lys Arg Glu Met Ser Ser Lys Thr Ile Pro
             20                  25                  30

Glu Leu Leu Lys Trp Ile Glu Asp Gly Ile Pro Lys Asp Pro Phe Leu
         35                  40                  45

Asn Pro Asp Leu Met Lys Asn Asn Pro Trp Val Glu Lys Ala Lys Cys
     50                  55                  60

Thr Ile Leu
 65

<210> SEQ ID NO 3
<211> LENGTH: 346
<212> TYPE: DNA
<213> ORGANISM: Mus musculus
<220> FEATURE:
<221> NAME/KEY: CDS
<222> LOCATION: (90)..(293)
<220> FEATURE:
<223> OTHER INFORMATION: gamma13 clone 2

<400> SEQUENCE: 3
gactccacag atccctcggc ccttgtcatc tctgcttttg ctgtctcctc caaaacctca    60
ggctggctac caccgacgcc cccgacgcc atg gag gag tgg gat gtg ccc cag    113
                                 Met Glu Glu Trp Asp Val Pro Gln
                                  1               5 atg aag aag gag gta gag agc ctc aag tac caa ctg gcc ttc aag agg    161
Met Lys Lys Glu Val Glu Ser Leu Lys Tyr Gln Leu Ala Phe Lys Arg
         10                  15                  20 gag atg tcg tcc aag acc atc ccc gag ctt ctc aag tgg att gag gat    209
Glu Met Ser Ser Lys Thr Ile Pro Glu Leu Leu Lys Trp Ile Glu Asp
     25                  30                  35              40 gga atc ccc aag gac ccc ttc ctg aac cca aac ctg atg aag aac aac    257
Gly Ile Pro Lys Asp Pro Phe Leu Asn Pro Asn Leu Met Lys Asn Asn
             45                  50                  55 cct tgg gta gag aag gcc aag tgc acc atc cta tga gcctgaccca         303
Pro Trp Val Glu Lys Ala Lys Cys Thr Ile Leu
         60                  65 cactctctgt aaggtgtgac tttataaata gacttctccg ggt                    346

<210> SEQ ID NO 4
<211> LENGTH: 67
<212> TYPE: PRT
<213> ORGANISM: Mus musculus
```

-continued

```
<400> SEQUENCE: 4

Met Glu Glu Trp Asp Val Pro Gln Met Lys Lys Glu Val Glu Ser Leu
 1               5                  10                  15

Lys Tyr Gln Leu Ala Phe Lys Arg Glu Met Ser Ser Lys Thr Ile Pro
             20                  25                  30

Glu Leu Leu Lys Trp Ile Glu Asp Gly Ile Pro Lys Asp Pro Phe Leu
         35                  40                  45

Asn Pro Asn Leu Met Lys Asn Asn Pro Trp Val Glu Lys Ala Lys Cys
     50                  55                  60

Thr Ile Leu
 65

<210> SEQ ID NO 5
<211> LENGTH: 370
<212> TYPE: DNA
<213> ORGANISM: Rattus norvegicus

<400> SEQUENCE: 5 ttttttttt tttttttggg atgtaccaag gcagagactc ctgagaagtc tgtttataaa      60
gtcacacctt aacagagagt gcgggtcagg ctcaaaggat ggtacacttg gccttctcca   120
cccaagggtt gttcttcatc aagtccgggt tcaagaaggg gtccttgggg atcccgtcct   180
caatccactt gaggagctcg gggatggtct tggatgacat ctccctcttg aaggccagtt   240
ggtacttgtg gctctccacc tccttcttca tctgggcac atcccactcc tccatggcgt    300
ctggggcgtc ggaggtagcc agcctgaggt tttgaaggag acagcaaaag cagagatgac   360
cctcgtgccg                                                           370

<210> SEQ ID NO 6
<211> LENGTH: 949
<212> TYPE: DNA
<213> ORGANISM: Homo sapiens
<220> FEATURE:
<221> NAME/KEY: CDS
<222> LOCATION: (69)..(272)

<400> SEQUENCE: 6
gttgtcattg tccctccgct gtcacctttt caagccccag gctggctgct tcagaagccc      60 ctgacccc atg gag gag tgg gac gtg cca cag atg aag aaa gag gtg gag     110
         Met Glu Glu Trp Asp Val Pro Gln Met Lys Lys Glu Val Glu
          1               5                  10 agc ctt aag tac cag ctg gcc ttc cag cgg gag atg gcg tcc aag acc      158
Ser Leu Lys Tyr Gln Leu Ala Phe Gln Arg Glu Met Ala Ser Lys Thr
 15                  20                  25                  30 atc ccc gag ctg ctg aag tgg atc gag gac ggg atc ccc aag gac ccc     206
Ile Pro Glu Leu Leu Lys Trp Ile Glu Asp Gly Ile Pro Lys Asp Pro
                 35                  40                  45 ttc ctg aac ccc gac ctg atg aag aac aac cca tgg gtg gaa aag ggc     254
Phe Leu Asn Pro Asp Leu Met Lys Asn Asn Pro Trp Val Glu Lys Gly
             50                  55                  60 aaa tgc acc atc ctg tga gccccgcacc cggcccctct cacaccatcc             302
Lys Cys Thr Ile Leu
         65 tgtgagacca cgcccggccc cactcccacc atcttgtaag actgtgccca gccccactca    362 ctccatcctg tgagtcccac tcccagcccc actcccacca tcctgtgagc ccatgcccgg    422 ccccactcac accaacctgt gagcccccact cccggcccca ctcactccat cttgtaagac   482 tatgcccagc cccattcact ccatcctgtg agtcccactc ccagccccac tcccaccatc    542
```

```
ctgtgagccc cacttccagc cccactccca ccatcctgtg agccccactc ccagccccac      602
tcccaccatc ctgtgagccc cactcccggc cccactcact ccatcctgtg agccccactc      662
ccagccccac tcacaccaac ctgtgagccc cactcccggc cccactcaca acatcttgta      722
agactgtgcc cggccccatt cactccatcc tgtgagacca cgcccggccc cactcactct      782
atcctgtgag accacgcctg gccccactcc caccatcctg tgagcccac tcctggcccc       842 actcacacca tcctatgagc ccacgcccgg ccccactccc accatcctgt gaaccccact      902
ccactcgcac gtgattacag tctgtaaagg tgtgacttta taaagac                   949
```

<210> SEQ ID NO 7
<211> LENGTH: 67
<212> TYPE: PRT
<213> ORGANISM: Homo sapiens

<400> SEQUENCE: 7

Met Glu Glu Trp Asp Val Pro Gln Met Lys Lys Glu Val Glu Ser Leu
 1               5                  10                  15

Lys Tyr Gln Leu Ala Phe Gln Arg Glu Met Ala Ser Lys Thr Ile Pro
            20                  25                  30

Glu Leu Leu Lys Trp Ile Glu Asp Gly Ile Pro Lys Asp Pro Phe Leu
        35                  40                  45

Asn Pro Asp Leu Met Lys Asn Asn Pro Trp Val Glu Lys Gly Lys Cys
    50                  55                  60

Thr Ile Leu
 65

<210> SEQ ID NO 8
<211> LENGTH: 3840
<212> TYPE: DNA
<213> ORGANISM: Homo sapiens
<220> FEATURE:
<221> NAME/KEY: CDS
<222> LOCATION: (2176)..(2274)
<220> FEATURE:
<221> NAME/KEY: CDS
<222> LOCATION: (2430)..(2534)
<220> FEATURE:
<221> NAME/KEY: intron
<222> LOCATION: (1)..(252)
<220> FEATURE:
<221> NAME/KEY: intron
<222> LOCATION: (588)..(2141)
<220> FEATURE:
<221> NAME/KEY: intron
<222> LOCATION: (2274)..(2428)
<220> FEATURE:
<221> NAME/KEY: intron
<222> LOCATION: (3212)..(3840)
<220> FEATURE:
<221> NAME/KEY: misc_feature
<222> LOCATION: (253)..(587)
<223> OTHER INFORMATION: EXON 1
<220> FEATURE:
<221> NAME/KEY: misc_feature
<222> LOCATION: (2142)..(2273)
<223> OTHER INFORMATION: EXON 2
<220> FEATURE:
<221> NAME/KEY: misc_feature
<222> LOCATION: (2429)..(3211)
<223> OTHER INFORMATION: EXON 3

<400> SEQUENCE: 8

```
actctcctgc cctcgggagc tgccccgtgc cggccactgg tctgggaaca ggggatcggg       60
ctggagcagg gagctccaca gagccccggg gcccctagca gtaagaggct cacatcccag      120
```

```
ggtgagccac atggcccaca caggatgcct ctgtcagggg ggcacagctg agtgtcacct      180
gaaccctgca ggctgcagag gcttcagagg gcaaagggtc ccagccccat ccccactcct      240
cccggctggc caggacact ggaggggaa cccacccct caagtggaag gagacctctc         300
caccagggcc caagctggcc cctcagggaa aatggaccag cccacactg gcccctggct       360 gcatgtccat ccgctgggtg agcccagggg agggggcagc acaggctatc tctgggtca       420 gcccagccct gaggagggtg tggggcggc gccagggccc aggtggcggg aggggcgggg      480
cacagccagg gctctgcctg gcggactccc ggaacatcac ttggccctcg ctctcactcg      540
cggtcgcctg ccgttgtca ttgtccctcc gctgtcacct tttcaaggta ggtccgatga      600
acaggcgccc ggggctaggg agggcccgga ggccctcga ctctcagctg cccaggtca       660 gtcccctggg ctcaccctaa ctcccggggc gagggcagct gccccgcagg cagcaaaacc     720
caacccgagc cggtgctgca ggcagggagg cggctctcgc ggtgcggggg agctgtgtcc     780
atctgagcgc cgtgcgccgc ctgcagtgcc caccgagtcc cgtggctggg ggcgtccacg     840
gggtgcacgg ggtgggtggc caggcttggc ggcagctgcg cgaaggtagg gctgggcagc     900
aaggactggg ctgtgggcgg ggcgccaaca ccccgggcct gggaggaccc gcacgcagct    960
agtcctgcgc ccacggggct gagtgtaggg tctccgagaa aaggcctgca ccggggatgg    1020
gggcgggtag gggtgctgga actccagagt ctccggagg gaatcctctg catgaccctg     1080
atcactcccc cagaaacctg ccccgctcg ctccccggcc tcccacccca ctacgggcag    1140
accctctgct ggctgctggg agtctgccca attcaccacc gggaccccac cagcctcagg     1200
ccctgggccc ctccctaggt ggccggtgca gctgcacgac caaaggatgg ggagactgtt     1260
gggccaggag ccccttcac agccagaggc aggctcccg aaacttgacg ccaacccca       1320 cccaccctcc caaggttcag ccctgtctcc caaccttggg gacgggggcc agagttggga     1380
cggagtgagg gactccctgg gcccctggag tgggtagggg gagaggcagg gggcaaccca    1440 ccccacttg cctcgaactt gtggcagttc tgagggtgt caacctgtgg ctttcccagg      1500
ctggccacaa gcagaaagca cgcaggtaac gtgtgtggtt cccagacaca ctggggaccc    1560
aggggccacc cacagcccat atcccagact cgggtagtat agcctgagcc cccaagatcc    1620
tgagcacaca ccccacctgc cagagaagca aactgcagca gaacattcct gtccaggagt    1680
cctggctctg gactgggctc tgccatgcaa agcaaagggg cacacagcgg ggcggggcag    1740 gggccaccctc ctgaggacct cgccccacac ctcacaccgt ggtctgggtc agcctgcgtg   1800
ggcctcagtg ggagggtagg agctgggggc ctgccgtgct gagcacccctt tctcctgcct   1860 gcaagggatc ttcgtaaggt gtgggggcct atggggggagt agctgaggat gtaaagtttc   1920
ttgcagttaa ttagtcccag tgcaggaggc gggagctggg gccttgtggg aactcgctct    1980
gtgccctgca ccctagcaac gcctagggga ctggcccagg cagtggtgtg gactctcccc    2040
gcttcatcct gcgggttca gctcaggcct gcggggagca gcggggtgg ggactacagg     2100 ctggtggcct cggccctgtg gcttcctcct gtgccctcca gcccaggct ggctgcttca     2160 gaagcccctg acccc atg gag gag tgg gac gtg cca cag atg aag aaa gag     2211
                  Met Glu Glu Trp Asp Val Pro Gln Met Lys Lys Glu
                    1               5                  10 gtg gag agc ctc aag tac cag ctg gcc ttc cag cgg gag atg gcg tcc      2259
Val Glu Ser Leu Lys Tyr Gln Leu Ala Phe Gln Arg Glu Met Ala Ser
            15                  20                  25 aag acc atc ccc gag tgagtgcccc acctgcctga tttgcctctc atttgtctgc      2314
Lys Thr Ile Pro Glu
```

-continued

```
                    30
cctgcgctgg ctgctcattt ccatagccac gaccaccgcc gccgacaggc aggtgcagca     2374
ggaggccctc gggggtcagg tgccaccact cacctgccac ccgcccaccc gcagg ctg      2432
                                                              Leu ctg aag tgg atc gag gac ggg atc ccc aag gac ccc ttc ctg aac ccc      2480
Leu Lys Trp Ile Glu Asp Gly Ile Pro Lys Asp Pro Phe Leu Asn Pro
 35              40                  45                  50 gac ctg atg aag aac aac cca tgg gtg gaa aag ggc aaa tgc acc atc      2528
Asp Leu Met Lys Asn Asn Pro Trp Val Glu Lys Gly Lys Cys Thr Ile
             55                  60                  65 ctg tga gccccgcacc cggcccctct cacaccatcc tgtgagacca cgcccggccc       2584
Leu cactcccacc atcttgtaag actgtgccca gccccactca ctccatcctg tgagtcccac    2644
tcccagcccc actcccacca tcctgtgagc ccatgcccgg ccccactcac accaacctgt    2704
gagccccact cccggcccca ctcactccat cttgtaagac tatgcccagc ccattcact     2764 ccatcctgtg agtcccactc ccagcccac tccaccatc ctgtgagccc cacttccagc      2824
cccactccca ccatcctgtg agccccactc ccagcccac tccaccatc ctgtgagccc      2884 cactccggc cccactcact ccatcctgtg agccccactc ccagcccac tcacaccaac      2944 ctgtgagccc cactcccggc cccactcaca acatcttgta agactgtgcc cggcccatt     3004 cactccatcc tgtgagacca cgcccggccc cactcactct atcctgtgag accacgcctg    3064
gccccactcc accatcctg tgagcccac tcctggcccc actcacacca tcctatgagc      3124
ccacgcccgg ccccactccc accatcctgt gaaccccact ccactcgcac gtgattacag    3184
tctgtaaagg tgtgactta taaagacatc tccagcttcc tgtctctgca ctctgcggga    3244
agcaatgcga gggcatgtcc gcggctcaga gaactagagc aagtccctga tgtacaggct    3304
gcgccgcacg gcgttggaga caccctcgtt gaagcggaac cagacctcgc tcctgcccac    3364
cgctgtgccc atgcgccgct ccactgagtc ctgctccggg gccgtgtccc ctgcggggcc    3424
acagggttgc tcctcagctg taaggcccc ccacaacccc caggccccc acaaccccac      3484 aacacccca cacacacctg cactcgggac tgctgtgctc ctgacgacca cacgtccaaa    3544
gaagtccttc tcaggctgat gggaggaagg actagtcagt cgtataggac agatgcccca    3604
tccagcccct acccaagaca ggaggaccga gagccttccc agggaggagg gaccagaaca    3664
cctctgagac acctttcgga acctggccca ggccagctgc ccctcaccc tcactgccat     3724 ctgctcccca ccaggtgcca atcaagaaga gccaatacag ccactcttct gcccagatgg    3784
gaaactgagg cctgggtaga accctggtca tgctgagggt aaggagctgg tccttc        3840
```

<210> SEQ ID NO 9
<211> LENGTH: 67
<212> TYPE: PRT
<213> ORGANISM: Homo sapiens

<400> SEQUENCE: 9

```
Met Glu Glu Trp Asp Val Pro Gln Met Lys Lys Glu Val Glu Ser Leu
 1               5                  10                  15

Lys Tyr Gln Leu Ala Phe Gln Arg Glu Met Ala Ser Lys Thr Ile Pro
             20                  25                  30

Glu Leu Leu Lys Trp Ile Glu Asp Gly Ile Pro Lys Asp Pro Phe Leu
         35                  40                  45

Asn Pro Asp Leu Met Lys Asn Asn Pro Trp Val Glu Lys Gly Lys Cys
     50                  55                  60
```

Thr Ile Leu
65

<210> SEQ ID NO 10
<211> LENGTH: 69
<212> TYPE: PRT
<213> ORGANISM: gamma8 cone

<400> SEQUENCE: 10

Met Ala Gln Asp Leu Ser Glu Lys Asp Leu Lys Met Glu Val Glu
1               5                   10                  15

Gln Leu Lys Lys Glu Val Lys Asn Thr Arg Ile Pro Ile Ser Lys Ala
            20                  25                  30

Gly Lys Glu Ile Lys Glu Tyr Val Glu Ala Gln Ala Gly Asn Asp Pro
        35                  40                  45

Phe Leu Lys Gly Ile Pro Glu Asp Lys Asn Pro Phe Lys Glu Lys Gly
        50                  55                  60

Gly Cys Leu Ile Ser
65

<210> SEQ ID NO 11
<211> LENGTH: 71
<212> TYPE: PRT
<213> ORGANISM: gamma2

<400> SEQUENCE: 11

Met Ala Ser Asn Asn Thr Ala Ser Ile Ala Gln Ala Arg Lys Leu Val
1               5                   10                  15

Glu Gln Leu Lys Met Glu Ala Asn Ile Asp Arg Ile Lys Val Ser Lys
            20                  25                  30

Ala Ala Ala Asp Leu Met Ala Tyr Cys Glu Ala His Ala Lys Glu Asp
        35                  40                  45

Pro Leu Leu Thr Pro Val Pro Ala Ser Glu Asn Pro Phe Arg Glu Lys
        50                  55                  60

Lys Phe Phe Cys Ala Ile Leu
65                  70

<210> SEQ ID NO 12
<211> LENGTH: 75
<212> TYPE: PRT
<213> ORGANISM: gamma4

<400> SEQUENCE: 12

Met Lys Glu Gly Met Ser Asn Asn Ser Thr Thr Ser Ile Ser Gln Ala
1               5                   10                  15

Arg Lys Ala Val Glu Gln Leu Lys Met Glu Ala Cys Met Asp Arg Val
            20                  25                  30

Lys Val Ser Gln Ala Ala Ser Asp Leu Leu Ala Tyr Cys Glu Ala His
        35                  40                  45

Val Arg Glu Asp Pro Leu Ile Ile Pro Val Pro Ala Ser Glu Asn Pro
        50                  55                  60

Phe Arg Glu Lys Lys Phe Phe Cys Thr Ile Leu
65              70                  75

<210> SEQ ID NO 13
<211> LENGTH: 73
<212> TYPE: PRT
<213> ORGANISM: gamma11

```
<400> SEQUENCE: 13

Met Pro Ala Leu His Ile Glu Asp Leu Pro Glu Lys Glu Lys Leu Lys
 1               5                  10                  15

Met Glu Val Glu Gln Leu Arg Lys Glu Val Lys Leu Gln Arg Gln Gln
                20                  25                  30

Val Ser Lys Cys Ser Glu Glu Ile Lys Asn Tyr Ile Glu Glu Arg Ser
            35                  40                  45

Gly Glu Asp Pro Leu Val Lys Gly Ile Pro Glu Asp Lys Asn Pro Phe
        50                  55                  60

Lys Glu Lys Gly Ser Cys Val Ile Ser
 65                 70

<210> SEQ ID NO 14
<211> LENGTH: 68
<212> TYPE: PRT
<213> ORGANISM: gamma7

<400> SEQUENCE: 14

Met Ser Ala Thr Asn Asn Ile Ala Gln Ala Arg Lys Leu Val Glu Gln
 1               5                  10                  15

Leu Arg Ile Glu Ala Gly Ile Glu Arg Ile Lys Val Ser Lys Ala Ser
                20                  25                  30

Ser Glu Leu Met Ser Tyr Cys Glu Gln His Ala Arg Asn Asp Pro Leu
            35                  40                  45

Leu Val Gly Val Pro Ala Ser Glu Asn Pro Phe Lys Asp Lys Lys Pro
        50                  55                  60

Cys Ile Ile Leu
 65

<210> SEQ ID NO 15
<211> LENGTH: 70
<212> TYPE: PRT
<213> ORGANISM: gamma8olf

<400> SEQUENCE: 15

Met Ser Asn Asn Met Ala Lys Ile Ala Glu Ala Arg Lys Thr Val Glu
 1               5                  10                  15

Gln Leu Lys Leu Glu Val Asn Ile Asp Arg Met Lys Val Ser Gln Ala
                20                  25                  30

Ala Ala Glu Leu Leu Ala Phe Cys Glu Thr His Ala Lys Asp Asp Pro
            35                  40                  45

Leu Val Thr Pro Val Pro Ala Ala Glu Asn Pro Phe Arg Asp Lys Arg
        50                  55                  60

Leu Phe Cys Thr Leu Leu
 65                 70

<210> SEQ ID NO 16
<211> LENGTH: 75
<212> TYPE: PRT
<213> ORGANISM: gamma3

<400> SEQUENCE: 16

Met Lys Gly Glu Thr Pro Val Asn Ser Thr Met Ser Ile Gly Gln Ala
 1               5                  10                  15

Arg Lys Met Val Glu Gln Leu Lys Ile Glu Ala Ser Leu Cys Arg Ile
                20                  25                  30

Lys Val Ser Lys Ala Ala Ala Asp Leu Met Thr Tyr Cys Asp Ala His
            35                  40                  45
```

```
Ala Cys Glu Asp Pro Leu Ile Thr Pro Val Pro Thr Ser Glu Asn Pro
         50                  55                  60

Phe Arg Glu Lys Lys Phe Phe Cys Ala Leu Leu
 65                  70                  75

<210> SEQ ID NO 17
<211> LENGTH: 74
<212> TYPE: PRT
<213> ORGANISM: gamma1

<400> SEQUENCE: 17

Met Pro Val Ile Asn Ile Glu Asp Leu Thr Glu Lys Asp Lys Leu Lys
 1               5                  10                  15

Met Glu Val Asp Gln Leu Lys Lys Glu Val Thr Leu Glu Arg Met Leu
                20                  25                  30

Val Ser Lys Cys Cys Glu Glu Phe Arg Asp Tyr Val Glu Glu Arg Ser
             35                  40                  45

Gly Glu Asp Pro Leu Val Lys Gly Ile Pro Glu Asp Lys Asn Pro Phe
         50                  55                  60

Lys Glu Leu Lys Gly Gly Cys Val Ile Ser
 65                  70

<210> SEQ ID NO 18
<211> LENGTH: 68
<212> TYPE: PRT
<213> ORGANISM: gamma5

<400> SEQUENCE: 18

Met Ser Gly Ser Ser Val Ala Ala Met Lys Lys Val Val Gln Gln
 1               5                  10                  15

Leu Arg Leu Glu Ala Gly Leu Asn Arg Val Lys Val Ser Gln Ala Ala
                20                  25                  30

Ala Asp Leu Lys Gln Phe Cys Leu Gln Asn Ala Gln His Asp Pro Leu
             35                  40                  45

Leu Thr Gly Val Ser Ser Thr Asn Pro Phe Arg Pro Gln Lys Val
         50                  55                  60

Cys Ser Phe Leu
 65

<210> SEQ ID NO 19
<211> LENGTH: 68
<212> TYPE: PRT
<213> ORGANISM: gamma10

<400> SEQUENCE: 19

Met Ser Ser Gly Ala Ser Ala Ser Ala Leu Gln Arg Leu Val Glu Gln
 1               5                  10                  15

Leu Lys Leu Glu Ala Gly Val Glu Arg Ile Lys Val Ser Gln Ala Ala
                20                  25                  30

Ala Glu Leu Gln Gln Tyr Cys Met Gln Asn Ala Cys Lys Asp Ala Leu
             35                  40                  45

Leu Val Gly Val Pro Ala Gly Ser Asn Pro Phe Arg Glu Pro Arg Ser
         50                  55                  60

Cys Ala Leu Leu
 65

<210> SEQ ID NO 20
<211> LENGTH: 72
```

```
<212> TYPE: PRT
<213> ORGANISM: gamma12

<400> SEQUENCE: 20

Met Ser Ser Lys Thr Ala Ser Thr Asn Asn Ile Ala Gln Ala Arg Arg
 1               5                  10                  15

Thr Val Gln Gln Leu Arg Met Glu Ala Ser Ile Glu Arg Ile Lys Val
                20                  25                  30

Ser Lys Ala Ser Ala Asp Leu Met Ser Tyr Cys Glu Glu His Ala Arg
            35                  40                  45

Asn Asp Pro Leu Leu Met Gly Ile Pro Thr Ser Glu Asn Pro Phe Lys
        50                  55                  60

Asp Lys Lys Thr Cys Thr Ile Leu
 65                  70
```

GUSTDUCIN γ SUBUNIT MATERIALS AND METHODS

The present application is a continuation of U.S. application Ser. No. 09/443,958, filed Nov. 19, 1999, now abandoned.

FIELD OF THE INVENTION

The present invention relates, in general, to materials and methods relevant to taste transduction. More particularly, the invention relates to the taste cell specific guanine nucleotide binding protein (G protein), gustducin, and to polynucleotide sequences encoding the gamma (γ) subunit of gustducin. The invention also relates to methods of modifying taste that involve agents which inhibit or activate the gustducin γ subunit, to methods for identifying such taste modifying agents and to the taste modifying agents.

BACKGROUND

Vertebrate taste transduction is mediated by specialized neuroepithelial cells, referred to as taste receptor cells. Groups of forty to one hundred taste receptor cells form a taste bud, the vast majority of which are embedded within the epithelium of the tongue. Each taste bud has a taste pore through which the taste receptor cells are exposed to the chemical environment in the mouth. Various taste stimulants (tastants) come into contact with the taste receptor cells and cause the taste receptor cells to send a signal to the brain by releasing neurotransmitter(s). Afferent nerve fibers that enter each taste bud receive the neurotransmitter signal.

There are four basic taste modalities typified by four distinct groups of tastants: salty, sour, sweet, and bitter. Different taste modalities appear to involve different signalling pathways and mechanisms. For example, salty taste appears to be mediated by sodium ion flux through apical sodium channels and sour taste seems to be mediated via hydrogen ion blockade of potassium or sodium channels.

Of particular interest to the background of the present invention are guanine nucleotide binding proteins (G proteins) which have been specifically implicated in the transduction of sweet and bitter tastes and may also be involved in the regulation of the ion channels involved in transduction of salty and sour tastes. Briefly, G proteins are heterotrimeric proteins (each having an α, β, and γ subunit) which mediate signal transduction in olfactory, visual, hormonal and neurotransmitter systems. G proteins couple cell surface receptors to cellular effector enzymes (e.g., phosphodiesterases and adenylate cyclase) or ion channels and thereby transduce an extracellular signal into an intracellular second messenger (e.g., cAMP, cGMP, $IP_3$). G protein α and βγ subunits separately and jointly regulate the activity of effector enzymes. Downstream events initiated by the effector enzymes result in release of neurotransmitter from the taste receptor cells. While the α subunit of a G protein is thought to confer most of the specificity of interaction between its receptor and its effectors, βγ dimers also contribute to the specificity of receptor coupling and to the regulation of receptor phosphorylation and desensitization. A number of G proteins are ubiquitously expressed (e.g., $G_s$ and $G_i$), but others that are known to be involved in sensory transduction have been found only in specialized sensory cells. For example, Lerea et al., *Science*, 224: 77–80 (1986) reports that transducin ($G_t$) transduces photoexcitation in retinal rod and cone cells and Ruiz-Avila et al., *Nature*, 376: 80–85 (1995) describes its participation in transduction of bitter taste in taste receptor cells. Jones et al., *Science*, 244: 790–795 (1989) reports that $G_{olf}$ transduces olfactory stimulation in neurons of the olfactory epithelium. The ubiquitously expressed G proteins may also be involved in sensory transduction.

Experimental evidence that G proteins are involved in the taste transduction pathway is described in several publications, including publications authored by co-inventors herein. Wong et at., *Cold Spring Harb. Symp. Quant. Biol.*, 61, 173–184 (1996) demonstrates the role of a G protein, gustducin, in bitter and sweet taste transduction. The article reports behavioral studies revealing that mice which do not express the gustducin α subunit exhibit insensitivity to various bitter and sweet compounds in comparison to normal mice. Moreover, the article reports that the mice exhibited significant descreases in nerve responses to the bitter and sweet compounds indicating that the bitter and sweet taste signalling pathway(s) had been interrupted by lack of expression of the gustducin α subunit. The gustducin α subunit has been described in terms of its DNA and amino acid sequences in U.S. Pat. No. 5,688,662 to Robert F. Margolskee. However, the β and γ subunits of the heterotrimeric gustducin G protein had not been previously identified or characterized.

Over the past two decades substantial efforts have been directed to the development of various agents that interact with taste receptors to mimic or block natural taste stimulants. Examples of agents that have been developed to mimic sweet tastes are saccharin (an anhydride of o-sulfimide benzoic acid) and monellin (a protein) and the thaumatins (also proteins). Thaumatins have been utilized as additives in food, cigarette tips, medicines and toothpaste. Many taste-mimicking or taste-blocking agents developed to date are not suitable as food additives, however, because either they are not economical or are high in calories, or because they are carcinogenic. Development of new agents that mimic or block the four basic taste modalities has been limited by a lack of knowledge of the taste receptor cell proteins responsible for transducing the taste modalities.

There thus continues to exist a need in the art for new products and methods that are involved in or affect taste transduction.

SUMMARY OF THE INVENTION

The present invention provides products and methods that are involved in or that affect taste transduction. In one of its aspects, the present invention provides purified and isolated polynucleotide sequences (e.g., DNA sequences and RNA transcripts including splice variants thereof, both sense and antisense strands) encoding the γ subunit of a novel taste receptor cell expressed G protein, gustducin, or fragments and variants of the γ subunit that possess at least one binding activity or immunological property specific to gustducin.

DNA sequences of the invention include genomic and cDNA sequences as well as wholly or partially chemically synthesized DNA sequences. Genomic DNA comprises the protein coding region for a polypeptide of the invention and includes allelic variants of the preferred polynucleotide of the invention. Allelic variants are known in the art to be modified forms of a wild type gene sequence, the modification resulting from recombination during chromosomal segregation or exposure to environmental conditions which give rise to genetic mutation. Allelic variants, like wild type genes, are inherently naturally occurring sequences (as opposed to non-naturally occurring variants which arise from in vitro manipulation). cDNA is obtained through reverse transcription of an RNA polynucleotide encoding gustducin γ subunit, followed by second strand synthesis of a complementary strand to provide a double stranded DNA. "Chemically synthesized" as used herein and understood in the art, refers to polynucleotides produced by purely chemical, as opposed to enzymatic, methods. "Wholly" chemically synthesized DNA sequences are therefore produced entirely by chemical means, and "partially" synthesized DNAs embrace those wherein only portions of the resulting DNA were produced by chemical means.

Preferred DNA sequences encoding a human gustducin γ subunit polypeptide are set out in SEQ ID NOs: 6 (cDNA) and 8 (genomic DNA). The worker of skill in the art will readily appreciate that the preferred DNA of the invention comprises a double stranded molecule, for example, the molecule having the sequence set forth in SEQ ID NO: 6 along with the complementary molecule (the "non-coding strand" or "complement") having a sequence deducible from the sequence of SEQ ID NO: 6 according to Watson-Crick base pairing rules for DNA. In addition, single-stranded polynucleotides, including single-stranded RNA as well as coding and noncoding DNA, are embraced by the invention. Also preferred are polynucleotides encoding the human gustducin γ subunit polypeptide of SEQ ID NO: 7.

The invention further embraces polynucleotides isolated from other species, such as the mouse and rat, which have sequence identity with human gustducin γ subunit DNA. Percent sequence "identity" with respect to polynucleotides of the invention is defined herein as the percentage of nucleotide bases in the candidate sequence that are identical to nucleotides in the CCR11 sequence after aligning the sequences and introducing gaps, if necessary, to achieve the maximum percent sequence identity. Exemplifying gustducin γ subunit polynucleotide sequences of the invention are the mouse cDNA sequences set out in SEQ ID NOs: 1 and 3 and the rat cDNA sequence set out in SEQ ID NO: 5.

The polynucleotide sequence information provided by the invention makes possible large scale expression of the encoded gustducin γ subunit polypeptide by techniques well known and routinely practiced in the art. Polynucleotides of the invention also permit identification and isolation of polynucleotides encoding related gustducin γ subunit polypeptides by well known techniques including Southern and/or Northern hybridization, polymerase chain reaction (PCR), and variations of PCR. Examples of related polynucleotides include human and non-human genomic sequences, including allelic variants, as well as polynucleotides encoding polypeptides homologous to gustducin γ subunit and structurally related polypeptides sharing one or more binding and/or immunological properties of gustducin γ subunit.

The disclosure of a full length polynucleotide encoding a gustducin γ subunit polypeptide makes readily available to the worker of ordinary skill in the art every possible fragment of the full length polynucleotide. The invention therefore provides fragments of gustducin γ subunit-encoding polynucleotides comprising at least 10 to 20, and preferably at least 15, consecutive nucleotides of a polynucleotide encoding gustducin γ subunit. Polynucleotides fragments of the invention comprise sequences unique to the gustducin γ subunit-encoding polynucleotide and are not identical to a corresponding fragment of a polynucleotide encoding any other γ subunit. The polynucleotide fragments hybridize under highly stringent or moderately stringent conditions only (i.e., "specifically" or "exclusively") to polynucleotides encoding gustducin γ subunit or gustducin γ subunit fragments. Polynucleotide fragments of genomic sequences of the invention comprise not only sequences unique to the coding region, but also include fragments of the full length sequence derived from introns, regulatory regions, and/or other non-translated sequences. Sequences unique to polynucleotides of the invention are recognizable through sequence comparison to other known γ polynucleotide sequences, and can be identified through use of alignment programs routinely utilized in the art.

Polynucleotide fragments of the invention are particularly useful as probes for detection of full length or fragment gustducin γ subunit polynucleotides. One or more polynucleotide fragments can be included in kits that are used to detect the presence of a polynucleotide encoding gustducin γ subunit, or used to detect variations in a polynucleotide sequence encoding gustducin γ subunit, including polymorphisms, and particularly single nucleotide polymorphisms. Kits of the invention optionally include a container and/or a label.

The invention embraces DNA sequences encoding gustducin γ subunit polypeptides that hybridize under highly or moderately stringent conditions to the non-coding strand, or complement, of the polynucleotide in SEQ ID NO: 6. Gustducin γ subunit-encoding polynucleotides of the invention include a) the polynucleotide set out in SEQ ID NO: 6; b) polynucleotides encoding a polypeptide encoded by the polynucleotide of (a), and c) polynucleotides that hybridize to the complement of the polynucleotides of (a) or (b) under conditions of moderate or high stringency. Exemplary high stringency conditions include a final wash in 0.2×SSC/0.1% SDS at 65° C. to 75° C., and exemplary moderate stringency conditions include a final wash at 2× to 3×SSC/0.1% SDS at 50° C. It is understood in the art that conditions of equivalent stringency can be achieved through variation of temperature and buffer, or salt concentration as described in Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

Knowledge of gustducin γ subunit-encoding DNA sequences allows for modification of cells to permit, or increase, expression of endogenous gustducin γ subunit. Cells can be modified (e.g., by homologous recombination) to provide increased gustducin γ subunit expression by replacing, in whole or in part, the naturally occurring gustducin γ subunit promoter (see the 5' noncoding sequences of gustducin γ subunit, nucleotides 1 to 2175 of SEQ ID NO: 8) with all or part of a heterologous promoter so that the cells express gustducin γ subunit at higher levels. The heterologous promoter is inserted in such a manner that it is operatively linked to ustducin γ subunit-encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the gustducin γ subunit coding sequence, amplification of the marker DNA by standard selection methods results in coamplification of the gustducin γ subunit coding sequences in the cells.

The DNA sequence information provided by the present invention also makes possible the development through, e.g. homologous recombination or "knock-out" strategies as disclosed in Capecchi, *Science* 244:1288–1292 (1989), of animals that fail to express functional gustducin γ subunit or that express a variant of gustducin γ subunit. Such animals are useful as models for studying the in vivo activities of gustducin γ subunit and modulators of gustducin γ subunit.

According to another aspect of the invention, host cells, especially unicellular eucaryotic and procaryotic cells, are stably transformed or transfected with the polynucleotide sequences of the invention in a manner allowing the expression of gustducin γ subunit polypeptides in the cells. Host cells expressing gustducin γ subunit polypeptide products, when grown in a suitable culture medium, are particularly useful for the large scale production of gustducin γ subunit polypeptides, fragments and variants; thereby enabling the isolation of the desired polypeptide products from the cells or from the medium in which the cells are grown.

The invention provides purified and isolated mammalian gustducin γ subunit polypeptides encoded by a polynucleotide of the invention. Presently preferred is a human gustducin γ subunit polypeptide comprising the amino acid sequence set out in SEQ ID NO: 7. The invention also embraces gustducin γ subunit polypeptides including fragment and variant polypeptides that are encoded by a DNA selected from the group consisting of: a) the polynucleotide set out in SEQ ID NO: 6; b) polynucleotides encoding a polypeptide encoded by the polynucleotide of (a), and c) polynucleotides that hybridize to the complement of the polynucleotides of (a) or (b) under moderate or high stringency conditions.

The invention also embraces polypeptides have at least 99%, at least 95%, at least 90%, at least 85%, at least 80%, at least 75%, at least 70%, at least 65%, at least 60% or at least 55% identity and/or homology to SEQ ID NO: 7. Percent amino acid sequence "identity" is defined herein as the percentage of amino acid residues in the candidate sequence that are identical with the residues in the gustducin γ subunit sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the gustducin γ subunit sequence after aligning the sequences and introducing gaps, if necessary, to achieve the maximum percent sequence identity, and also considering any conservative substitutions as part of the sequence identity.

Polypeptides of the invention may be isolated from natural cell sources or may be chemically synthesized, but are preferably produced by recombinant procedures involving host cells of the invention. Use of mammalian or insect host cells is expected to provide for such post-translational modifications (e.g., glycosylation, truncation, lipidation, and phosphorylation) as may be needed to confer optimal biological activity on recombinant expression products of the invention.

Gustducin γ subunit polypeptides of the invention include fragments and variants, and variant fragments. Variants and variant fragments may comprise polypeptides wherein one or more of the specified amino acids is deleted (i.e., polypeptide fragments) or replaced and/or wherein one or more nonspecified amino acids are added: (1) without loss, and preferably with enhancement, of one or more of the binding activities or immunological properties specific for gustducin; or (2) with specific disablement of a particular binding function. The invention contemplates gustducin γ subunit polypeptides having combinations of insertions, deletions and/or substitutions. Polypeptide fragments of the invention retain binding and/or immunological properties unique or specific to the gustducin γ subunit. Fragments comprising at least 5, 10, 15, 20, 25, 30, 35, or 40 consecutive amino acids of SEQ ID NO: 7 are comprehended by the invention.

Also contemplated by the present invention are antibody substances (e.g., monoclonal and polyclonal antibodies, chimeric and humanized antibodies, and antibody domains including Fab, Fab', F(ab')$_2$ and single chain domains, and Fv or single variable domains) which are specific for the gustducin γ subunit. The term "specific for" indicates that the variable regions of the antibodies of the invention recognize and bind gustducin γ subunit polypeptides exclusively (i.e., are able to distinguish gustducin γ subunit polypeptides from the other members of the family of γ subunits despite sequence identity or homology among the family), but may also interact with other proteins (for example, *S. aureus* protein A or other antibodies in ELISA techniques) through outside the variable or CDR regions of the antibodies, and in particular, in the constant region of the molecule. Screening assays to determine binding specificity or exclusivity of an antibody of the invention are well known and routinely practiced in the art. Antibodies that recognize and bind fragments of the gustducin γ subunit polypeptides of the invention are also contemplated, provided that the antibodies are first and foremost specific or exclusive for, as defined above, gustducin γ subunit polypeptides. Antibody substances can be developed using isolated natural or recombinant gustducin γ subunit polypeptide products or host cells expressing such products on their surfaces by methods standard in the art. The antibody substances may be utilized for purifying polypeptides of the invention and for blocking or inhibiting binding activities of gustducin.

Yet another aspect of the present invention relates the observation that gustducin γ subunit polypeptides are particularly suited for use in methods for identifying taste modifying agents. Methods of identifying taste modifying agents according to the invention generally involve testing an agent for the capability to mimic or inhibit the interaction of gustducin βγ dimer with the gustducin α subunit and/or sensory receptor, to mimic or inhibit the interation of the gustducin γ subunit with a G protein β subunit, or to mimic or inhibit the interaction of gustducin βγ dimer with an effector enzyme.

A first preferred method for identifying a taste modifying agent comprises the steps of incubating phospholipid vesicles having gustducin γ subunit associated in biologically active form with a G protein β subunit and gustducin α subunit or transducin α subunit, adding radioactively labeled GTPγS in the presence and absence of an agent, and measuring the rate of GTPγS binding by the α subunit in the presence of the agent compared to the rate in the absence of the agent. An increase in the rate of binding indicates that the agent is a taste stimulator and a decrease in the rate of binding indicates that the agent is a taste inhibitor.

A second preferred method for identifying a taste modifying agent includes the steps of incubating phospholipid vesicles having gustducin γ subunit associated in biologically active form with a G protein α subunit and gustducin β subunit or transducin α subunit, adding GTP in the presence and absence of an agent, and measuring the rate of conversion of GTP to GDP by the α subunit in the presence of the agent compared to the rate in the absence of the agent. An increase in the rate of conversion indicates that the agent is a taste stimulator and a decrease in the rate of conversion indicates that the agent is a taste inhibitor.

A third preferred method for identifying a taste modifying agent comprises the steps of incubating activated gustducin γ associated in biologically active form with a G protein β subunit and phospholipase C, adding $^3$H-myoinositol in the presence and absence of an agent, and measuring inositol trisphosphate generation in the presence of the agent in comparison to in the absence of the agent. An increase in inositol trisphosphate generation indicates the agent is a taste stimulator and a decrease in inositol trisphosphate generation indicates that the agent is a taste inhibitor.

In the above methods, either phospholipid vesicles comprising recombinant taste receptors or phospholipid vesicles containing reconstituted crude taste receptors from animal or human sources may be used instead of phospholipid vesicles without taste receptors.

Taste modifying agents may, for example, comprise a gustducin γ subunit fragment peptide possessing at least one binding activity specific to the γ subunit of gustducin. Presently preferred taste modifying peptides include: a) peptides comprising about amino acid 1 through about amino acid 14 of SEQ ID NO: 7, b) peptides comprising about amino acid 18 through about amino acid 32 of SEQ ID NO: 7, c) peptides comprising about amino acid 31 through about amino acid 40 of SEQ ID NO: 7, d) peptides comprising about amino acid 47 through amino acid 59 of SEQ ID NO:, and e) peptides comprising about amino acid 56 through about amino acid 67 of SEQ ID NO: 7. The peptides may be acetylated at the amino terminus or amidated at the carboxyl terminus. Preferably, peptides of e) are lipid modified (e.g., farnesylated or geranylgeranylated).

Other peptides which bind to the gustducin γ subunit may be identified by contacting gustducin γ subunits with peptides and isolating the peptides which bind to the subunits. Appropriate peptide display libraries or phage epitope libraries which may be utilized in such methods are described in Scott et al., *Science,* 249: 386–390 (1990); Lam et al., *Nature,* 354: 82–84 (1991); and Houghton et al., *Nature,* 354: 84–86 (1991).

Taste modifying agents according to the invention may also comprise proteins or peptides which specifically bind to a gustducin γ subunit-encoding nucleic acid, oligonucleotides which bind to a gustducin γ subunit polypeptide or a gustducin γ subunit gene sequence, and other non-peptide compounds (e.g., isolated or synthetic organic and inorganic molecules) which specifically react with a gustducin γ subunit polypeptide or encoding nucleic acid. There are a number of different libraries used for the identification of small molecule modulators, including, (1) chemical libraries, (2) natural product libraries, and (3) combinatorial libraries comprised of random peptides, oligonucleotides or organic molecules. Chemical libraries consist of structural analogs of known compounds or compounds that are identified as "hits" or "leads" via natural product screening. Natural product libraries are collections from microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see *Science* 282:63–68 (1998). Combinatorial libraries are composed of large numbers of peptides, oligonucleotides or organic compounds as a mixture. They are relatively easy to prepare by traditional automated synthesis methods, PCR, cloning or proprietary synthetic methods. Of interest are peptide and oligonucleotide combinatorial libraries. Still other libraries of interest include peptide, protein, peptidomimetic, multiparallel synthetic collection, recombinatorial, and polypeptide libraries.

Taste modifying agents of the invention bind specifically or exclusively to a gustducin γ subunit polypeptide or a gustducin γ subunit-encoding polynucleotide as defined above and include taste modifying agents that bind a gustducin γ subunit polypeptide or a gustducin γ subunit-encoding polynucleotide with higher affinity or avidity compared to other compounds are also contemplated. Variant gustducin γ subunit polypeptides which affect the binding activity or cellular localization of wild-type gustducin γ subunit polypeptides are also contemplated by the invention. Presently preferred targets for the development of selective taste modifying agents include, for example: (1) regions of gustducin γ subunit that contact other proteins (e.g., taste receptors, α subunits, β subunits and effectors), (2) regions that localize gustducin γ subunit within a cell, (3) allosteric regulatory binding site(s) of gustducin γ subunit, and (5) post-translational modification site(s) of gustducin γ subunit as well as other regions of the protein wherein covalent modification regulates biological activity.

BRIEF DESCRIPTION OF THE DRAWINGS

FIG. 1 is an alignment of the amino acid sequence of the γ subunits including the murine gustducin γ subunit (SEQ ID NO: 2), human gustducin γ subunit (SEQ ID NO: 7), γ8cone (SEQ ID NO: 10), γ2 (SEQ ID NO: 11), γ4 (SEQ ID NO: 12), γ11 (SEQ ID NO: 13), γ7 (SEQ ID NO: 14), γ8olf (SEQ ID NO: 15), γ3 (SEQ ID NO: 16), γ1 (SEQ ID NO: 17), γ5 (SEQ ID NO: 18), γ10 (SEQ ID NO: 19), and γ12 (SEQ ID NO: 20).

According to another aspect of the present invention, taste modifying agents are delivered to taste receptor cells to modify taste (i.e., mimic or inhibit sweet and/or bitter tastes). The agents may be additives to any substance orally consumed or applied.

DETAILED DESCRIPTION

Numerous aspects and advantages of the present invention will be apparent upon consideration of the illustrative examples and descriptions in the following detailed description thereof, reference being made to FIG. 1.

The present invention is illustrated by the following examples wherein Example 1 describes the cloning of DNA sequences encoding the γ subunit of mouse, rat and human gustducin; Example 2 presents an analysis of the gustducin γ subunit amino acid sequence; Example 3 describes the results of Northern blot and in situ hybridizations examining the tissue and cell expression of gustducin γ subunit; Example 4 describes the generation of gustducin γ subunit specific polyclonal antibodies; Example 5 presents results of immunocytochemistry experiments showing the concomitant expression of gustducin α and γ subunits in taste receptor cells; Example 6 describes the interaction as measured by trysin protection assays of gustducin γ subunit with Gβ subunits, Gβ subunits and receptors; Example 7 presents assays demonstrating gustducin γ subunit participation in bitter taste transduction; and Example 8 describes methods for identifying taste modifying agents having the capability to affect interactions between the gustducin γ subunit and effectors and also describes methods for utilizing such taste modifying agents to modify taste by mimicking or inhibiting sweet or bitter tastes.

EXAMPLE 1

Gustducin γ subunit DNA was isolated by reverse transcription-polymerase chain reaction (RT-PCR) on single taste receptor cells, followed by differential screening of cDNA libraries from single taste cells.

Briefly, individual taste receptor cells were isolated by limited enzymatic dispersal of circumvallate papillae from transgenic mice that express a green fluorescent protein (GFP) transgene from the gustducin promoter. Live GFP-positive taste receptor cells were identified by their green fluorescence, while live GFP-negative taste receptor cells were picked according to their bipolar morphology and lack of green fluorescence. Messenger RNA from each single taste cell was reverse transcribed into cDNA, which was then amplified by PCR. PCR products were divided into three portions for the following uses: (a) target DNA for profiling gene expression; (b) single cell cDNA library construction; (c) generation of probes with which to differentially screen single cell cDNA libraries.

The cDNA library from a GFP-positive (i.e., α-gustducin-expressing) cell was screened with "self probe" (the PCR products from the same cell) and "non-self probe" (the PCR products from a GFP-negative taste cell). Of 40,000 plaques screened, 60 clones were self-probe-positive, but negative with the non-self probe. Two of these clones contained an open reading frame of 201 bp, predicted to encode a 67 amino acid long protein homologous to known G protein γ subunits. The DNA and deduced amino acid sequences of the mouse clone 1 (1qseq183) are set out in SEQ ID NOs: 1 and 2, while the DNA and deduced amino acid sequences of the mouse clone 2 (1qseq146) are set out in SEQ ID Nos: 3 and 4. There is one amino acid difference between the two sequences at position 51.

Using the open reading frame as a query sequence, a search of DNA sequence databases identified as homologous two partially sequenced EST clones from cDNA libraries of human brain and rat mixed organs. Neither clone was identified in the database as encoding a G protein γ subunit. The DNA sequence in the database for the rat EST clone (accession number AI454466) is set out in SEQ ID NO: 5. The human EST clone (accession number H46116) was ordered from the IMAGE Consortium and resequenced. Resequencing of the clone revealed various differences. Following the naming convention of γ subunits, the γ subunit encoded by the clone was designated Gγ13 but is referred to herein as the gustducin γ subunit. The DNA and deduced amino acid sequence of the resequenced clone are set out in SEQ ID NOs: 6 and 7. The rat and human clones respectively encode γ subunits with 98.5% and 95.5% amino acid identity to the sequence encoded by the mouse gustducin γ subunit clone. The predicted gustducin γ subunit protein is smaller in length than all other known γ subunits, with a calculated molecular weight of 7.9 kDa.

Searching databases of human genomic DNA with the human cDNA sequence (SEQ ID NO: 6) identified a clone from the telomeric region of the short arm of human chromosome 16 (16P13.3) (accession number AL031033) that contained the gustducin γ subunit transcript. The 949 base pair human coding DNA was distributed over 2.6 kb of genomic DNA. See SEQ ID NOs 8 and 9. Like other γ subunit genes, the gustducin γ subunit gene is composed of three exons and two introns: the first exon contains only the 5' flanking region, the second exon contains the translation initiation site and the codons for the first thirty-three amino acids, while the third exon contains the rest of the coding sequence and the 3' flanking region. The second intron of the gustducin γ subunit is shifted seven amino acids toward the carboxy terminus in comparison with γ subunit genes γ1, γ4, γ5, γ8cone, in which the second intron is precisely located two amino acid residues downstream of a highly conserved arginine residue. In the gustducin γ subunit amino acid sequence, SEQ ID NO: 8, the conserved arginine residue is at amino acid position 24.

EXAMPLE 2

Comparison of the Sequence of the Gustatory γ Subunit Clone with Known G Protein γ Subunits Alignment of the amino acid squence of the gustducin γ subunit with the published amino acid sequences of other γ subunits (FIG. 1) revealed that it is the most divergent member of the γ family, most similar to Gγ8cone (33% amino acid identity). See Table 1 below wherein the percent identity between subunits is shown above the diagonal and the percent similarity between subunits is shown below the diagonal.

TABLE 1

Amino acid relatedness of Gγ subunits

| | γ1 | γ2 | γ3 | γ4 | γ5 | γ7 | γ8cone | γ8olf | γ10 | γ11 | γ12 | γgust |
|---|---|---|---|---|---|---|---|---|---|---|---|---|
| γ1 | * | 33 | 30 | 31 | 27 | 38 | 62 | 31 | 31 | 73 | 34 | 25 |
| γ2 | 48 | * | 75 | 75 | 48 | 67 | 38 | 70 | 52 | 32 | 62 | 32 |
| γ3 | 46 | 87 | * | 68 | 46 | 58 | 33 | 56 | 51 | 28 | 56 | 28 |
| γ4 | 50 | 92 | 79 | * | 43 | 56 | 31 | 63 | 46 | 30 | 53 | 32 |
| γ5 | 46 | 76 | 71 | 73 | * | 49 | 28 | 45 | 53 | 26 | 44 | 24 |
| γ7 | 56 | 85 | 79 | 84 | 79 | * | 40 | 56 | 53 | 38 | 76 | 30 |
| γ8cone | 86 | 48 | 48 | 48 | 48 | 49 | * | 31 | 36 | 64 | 38 | 33 |
| γ8olf | 50 | 89 | 79 | 84 | 69 | 79 | 58 | * | 51 | 30 | 49 | 29 |
| γ10 | 53 | 71 | 71 | 68 | 79 | 76 | 48 | 62 | * | 31 | 41 | 24 |
| γ11 | 90 | 48 | 48 | 49 | 48 | 59 | 78 | 51 | 54 | * | 36 | 31 |
| γ12 | 54 | 76 | 76 | 76 | 76 | 91 | 49 | 80 | 69 | 57 | * | 27 |
| γgust | 49 | 46 | 46 | 48 | 39 | 45 | 46 | 48 | 40 | 51 | 49 | * |

EXAMPLE 3

Tissue Expression of the Gustducin γ Subunit

To examine the general distribution of expression of gustducin γ subunit in non-taste tissues, Northern blot analysis with human RNAs was carried out. DNA probes were generated by random primed radiolabeling of the human gustducin γ subunit cDNA. A Multiple Tissue Northern blot (Clontech) was hybridized sith the human sequence DNA probe. Each lane contained 1 μg of human poly A+RNA from PBL, lung, placenta, small intestine, liver, kidney, spleen, thymus, colon, skeletal muscle, heart and brain. The probes hybridized predominantly to a 1.2 kb mRNA in brain and weakly to a 6.2 kb mRNA from brain. The 1.2 kb mRNA was also present at low levels in small intestine and thymus. The higher molecular weight transcript could be the unprocessed primary RNA transcript.

To confirm that gustducin γ subunit was expressed in taste receptor cells, $^{33}$P-labelled RNA gustducin γ subunit probes generated by in vitro transcription in the presence of P-33 labeled UTP were used for in situ hybridization of frozen sections (8 μm) of mouse lingual tissue. Hybridization was performed in 10 mM Tris containing 0.6M NaCl, 0.02% Ficoll, 0.02% PVP, 1 mM EDTA, 0.1% BSA, 0.5 mg/ml salmon sperm DNA, 0.5 mg/ml yeast total RNA, 0.5 mg/ml yeast tRNA, 10% dextran sulphate 0.05 mg/ml polyadenylic acid, 0.1% SDS and 50% formamide at 50° C. for 12–14 hours in a humid chamber. Slides were washed sequentially in 2×SSC and 0.2×SSC at 55° C. for 1 hour each. Slides were coated with Kodak NTB-2 nuclear track emulsion and exposed at 4° C. for three weeks and then developed, fixed and stained. Gustducin γ subunit was selectively expressed in taste receptor cells, but absent from the surrounding lingual epithelium, muscle or connective tissue. Sense probe controls showed no non-specific hybridization to lingual tissue.

To determine which G protein subunits were expressed in taste bud-containing tissue, probes from the 3' flanking region of mouse gustducin γ subunit, gusducin α subunit, β1 and β3 cDNAs were hybridized to amplified cDNAs from a single circumvallate papilla or a similar-sized piece of non-gustatory lingual epithelium. Gustducin α subunit, β3 and gustducin γ subunit were only expressed in taste bud-containing tissue, while β1 was expressed in both gustatory and non-gustatory lingual epithelia. Next, the pattern of expression of gustducin γ subunit, gustducin α subunit and Gβ subunits in individual taste cells was examined. Single cell RT-PCR products of Example 1 were hybridized with the same set of G protein subunit probes. All of the cells that expressed gustducin α subunit also expressed gustducin γ subunit and β3. Most of the of the gustducin α subunit-positive cells also expressed β1.

EXAMPLE 4

Antibody substances (including monoclonal and polyclonal antibodies, chimeric and humanized antibodies, and antibody domains including Fab, Fab', F(ab')$_2$ and single chain domains, and Fv or single variable domains) that are specific for the gustducin γ subunit may be developed using isolated natural or recombinant gustducin γ subunit polypeptide products or host cells expressing such products on their surfaces. The antibody substances may be utilized for blocking or inhibiting the binding activities of gustducin and for purifying gustducin materials of the invention.

Murine gustducin γ subunit peptides respectively comprising amino acids 18–32 and 47–59 of SEQ ID NO: 1 were synthesized by Zymed Laboratories Inc. using Fmoc chemistry. The peptides were conjugated to keyhole limpet hemocyanin. The peptides were individually used to inoculate rabbits to raise polyclonal anti-peptide antisera specific for each peptide. On day 0, preimmune sera was collected from each rabbit and then the 0.5 mg of a peptide in Freund's Adjuvant was injected subcutaneously into each animal. On days 21 and 42, two boosters of 0.5 mg of a peptide in incomplete Freund's adjuvant (IFA) were injected subcutaneously. On day 52, a 8 ml sample of test antiserum was bleeded. On day 60, another booster was injected and on day 73, Fifty ml antiserum was collected from each animal.

EXAMPLE 5

To determine if the gustducin α and γ subunits colocalized to the same taste receptor cells, the polyclonal antisera was used to carry out immunocytochemistry on murine lingual epithelium. Three micron thick frozen sections of murine lingual tissue (previously fixed in 4% paraformaldehyde and cryoprotected in 20% sucrose) were blocked in 3% BSA, 0.3% Triton X-100, 2% goat serum and 0.1% Na Azide in PBS for 1 hour at room temperature and then incubated for 8 hours at 4° C. with purified antibody against gustducin α subunit or antiserum against gustducin γ subunit (1:1000), plus the appropriate secondary antibody. In some cases, the osculating faces of the adjacent sections were imaged, one of the images rotated 180° and superimposed with the other.

About one third of taste receptor cells in circumvallate, foliate and fungiform papillae were positive for either gustducin α subunit or γ subunit. Longitudinal sections of the γ subunit-positive taste cells displayed the elongated bipolar morphology typical of α subunit-positive cells. Analysis of adjacent transverse sections indicated that the vast majority of γ subunit-positive cells were α subunit-positive, and vice versa; the few exceptions were apparently due to the physical absence of particular taste cells in the adjacent section as the level of the section ascended above the cells' apical end. The osculating faces of two adjacent oblique sections were stained with the two types of antibodies, then the images were superimposed revealing fully coincident expression of the two G protein subunits.

These results are consistent with the expression profiling described in Example 3, and demonstrate that the gustducin α and γ subunits are expressed in the same subset of taste receptor cells.

EXAMPLE 6

Interaction with Gα Subunits

The colocalization of the gustducin α and γ subunits in taste receptor cells suggested their interaction to transduce taste receptor cell responses. The interaction was confirmed using a trypsin protection assay that detects the direct interaction of G protein α and γ subunits. The assay is based on the fact that γ subunits, in the absence of β subunits, can interact directly with α subunits, and that this interaction apparently dictates which βγ dimer associates with which α subunit. See Rahmatullah & Robishaw, *J. Biol. Chem.*, 269: 3574–3580 (1994).

To monitor G protein α and γ subunit interactions, gustducin γ and α subunit DNAs were transcribed and translated in vitro using the Promega TNT system, mixed in a 3:1 ratio, and incubated for 15 minutes at 30° C. in buffer G [15 mM Na-HEPES pH 8.0, 250 mM NaCl, 0.6 mM EDTA, 0.6 mM DTT, 5 mM MgCl$_2$, 0.1 mM GDP and 0.3% polyoxyethylene 10-lauryl ether (LPX)]. The assay was initiated by adding Tosyl-L-phenylalanine chloromethyl ketone (TPCK) treated-trypsin (0.5 µg), incubated for 1 hour at 30° C., and terminated with 3 µg soybean trypsin inhibitor (SBTI) (15 min, at 30° C.). The samples were analyzed on 12% SDS-PAGE, gels were fixed, enhanced with En$^3$Hance (NEN), dried and exposed to X-ray film.

Gustducin γ subunit protected gustducin α subunit from tryptic digestion to a significant extent. Other Gγ subunits were also tested in the assay. Gγ1, which interacts with the rod transducin α subunit, also appeared to interact with gustducin α subunit, albeit to a lesser extent. The cone γ8 subunit (the cone transducin α subunit partner) and Gγ5 were unable to protect the gustducin α subunit from trypsin digestion.

Interaction with Gβ Subunits

The expression of β3 and β1 in the gustducin α and γ subunit-expressing cells described in Example 3 suggested that these β subunits might interact with gustducin α subunit and γ subunit to form heterotrimers. To determine which β and gustducin γ subunit combinations were capable of forming dimers another trypsin assay was utilized. β monomers are cleaved at numerous sites by trypsin, whereas βγ dimers are cleaved at a single site, resulting in the appearance of a 26-kDa fragment of the β subunit. See Schmidt et al., *J. Biol. Chem.*, 267: 13807–13810 (1992).

Plasmid DNAs (0.5 µg) encoding β1 subunit was transcribed and translated in vitro, in the presence or absence of plasmid DNA (0.5 µg) coding for the gustducin γ subunit. Aliquots (10 µl) of the cotranslated βγ mix or β subunit alone were digested by TPCK-treated trypsin (1 µg) in a final volume of 20 µl (with 50 mM Na-HEPES pH 8.0). After incubation for 1 hour at 30° C., the digestions were stopped by addition of 6 µg SBTI as described above. Protected fragments of β subunits were analyzed on 15% SDS-PAGE. Detection was as described above.

In the assay, β1 formed dimers with gustducin γ subunit that were protected from trypsin digestion.

Interaction with Taste Receptors

Taken together, the trypsin assay results described above and the colocalization results described in Example 5 (interaction of gustducin γ and α subunits with β3 and β1 in taste receptor cells) suggested that gustducin γ subunit forms heterotrimers with gustducin α subunit and β3 or β1 to transduce taste responses. To confirm this idea, yet another trypsin sensitivity assay was utilized.

Five µl aliquots of in vitro translated gustducin α subunit were incubated with 5 µg of purified taste membranes or control non-taste membranes, 0.1 mM GDP, 1 µM GTPγS, with or without 5 mM of the bitter compound denatonium, plus a 10 µl aliquot of cotranslated β1/gustducin γ subunit or β2/γ2 dimer, or 10 µl rabbit reticulocyte lysate (the minus βγ control) for 1 hour at 30° C., followed by digestion with trypsin as described in Ming et al., *Proc. Natl. Acad. Sci. USA*, 95: 8933–8938 (1998).

The addition of β1/gustducin γ subunit enhanced activation of gustducin α subunit by taste receptor-containing membranes stimulated by denatonium. In contrast, β2/γ2 did not enhance activation. In control experiments, β1/gustducin γ subunit did not enhance activation of gustducin α subunit by non-taste membranes, i.e., the activation of α-gustducin required (1) taste receptor-containing membranes, (2) denatonium and (3) a gustducin γ subunit-containing βγ dimer. Hence, gustducin α subunit, β1 and gustducin γ subunit can associate with each other to form a functional heterotrimeric G protein capable of interacting with denatonium-responsive taste receptors. Moreover, the coincident expression of β3 and gustducin γ subunit with gustducin α subunit in the taste receptor cells suggests that they also form a heterotrimer in vivo.

EXAMPLE 7

To confirm that gustducin γ subunit does indeed function in taste transduction rapid time course quench-flow experiments were carried out essentially as described in Tarelius et al., pp. 193–202 in Spielman et al., Eds., *Experimental Cell Biology of Taste and Olfaction. Current Techniques & Protocols*, CRC Press, Boca Raton (1995). It has been shown previously in such experiments that denatonium and sucrose octa-acetate cause the rapid (50–200 msec) generation of inositol triphosphate (IP$_3$) in murine taste tissue, but not in control non-taste tissue. Furthermore, it has been shown that the denatonium response depends upon a novel phospholipase C (PLC) β2 isotype specifically expressed in taste receptor cells.

Tongues were excised from 6 to 8 week old female SWR mice, and lingual papillae removed. One vallate and two foliate papillae and nongustatory control tissue from the dorsal eminence of the peeled epithelium were placed in ice-cold MOPS buffer pH 6.9 (50 mM MOPS, 100 mM NaCl, 0.081 mM CaCl$_2$ and 2.5 mM MgCl$_2$), containing 10 mM EGTA, 1 mM DTT, and a protease inhibitor cocktail [1 mg/ml, specific for serine, cysteine, aspartic and metalloproteinases (Sigma)]. Tissue collected from twenty-five tongues was homogenized in MOPS-EGTA buffer pH 6.9, without the enzyme inhibitors, and centrifuged (1000×g for 20 min. at 4° C.). The recovered supernatant (at a protein concentration of about 30 µg/ml), was used for rapid kinetic experiments. The tissue was prepared fresh and kept at 4° C. prior to the quench flow experiment and loaded into the quench flow module (QFM) in small batches just seconds prior to injection.

The addition of denatonium benzoate to murine taste tissue induced the generation of IP$_3$ to slightly more than twice the basal level. IP$_3$ generation was not affected by the addition of either buffer or antibody alone. However, when the taste tissue was preincubated with either of two antisera (Example 4) to gustducin γ subunit, the addition of denatonium did not increase IP3 levels appreciably. In contrast, preincubation of the taste tissue with normal IgG did not reduce the denatonium-stimulated generation of IP$_3$. Likewise, preincubation with antibodies against γ1 or γ3 did not reduce denatonium-stimulated generation of IP$_3$. These results demonstrate that βγ subunit pairs containing the gustducin γ subunit mediate the denatonium-responsive activation of taste tissue PLC β2 to generate IP$_3$. Generation of IP$_3$ in taste receptor cells leads to increases in intracellular calcium ion levels which in turn leads to cell depolarization and release of neurotransmitter(s).

EXAMPLE 8

Gustducin γ subunits may be utilized in methods to identify taste modifying agents that are capable of mimicking, blocking or inhibiting particular tastes. As indicated below, the specific identification methods are designed by analogy to procedures employed to characterize activation and effector functions of known G proteins. The assays may also be used to test activity of gustducin γ polypeptides of the invention.

A first type of method identifies taste modifying agents that mimic or block the effect of an activated taste receptor on the gustducin or transducin α subunit. For example, one method contemplated by the invention is analogous to an assay described in Cheung et al., *FEBS Letters,* 279(2), 277–280 (1991) wherein evidence of peptide activation of various G proteins was an increase in the rate of GTPγS binding by G protein α subunits. (GTPγS is a nonhydrolyzable form of GTP.) The method therefore may include the steps of incubating incubating phospholipid vesicles having gustducin γ subunit associated in biologically active form with a G protein β subunit (e.g., Gβ1 or Gβ2) and gustducin α subunit (bound to GDP) or transducin α subunit (bound to GDP), adding radioactively labeled GTPγS in the presence and absence of an agent, and measuring the rate of GTPγS binding by the α subunit in the presence of the agent compared to the rate in the absence of the agent. An increase in the rate of binding indicates that the agent is a taste stimulator and a decrease in the rate of binding indicates that the agent is a taste inhibitor.

Another method of the first type is analogous to a different assay described in Cheung et al., *FEBS Letters,* 279(2), 277–280 (1991) wherein evidence of peptide activation of various G proteins was an increase in the rate of G protein α subunit GTPase activity. This method may therefore comprise the steps of incubating phospholipid vesicles having gustducin γ subunit associated in biologically active form with a G protein β subunit (e.g., Gβ1 or Gβ2) and gustducin α subunit (bound to GDP) or transducin α subunit (bound to GDP), adding GTP in the presence and absence of an agent, and measuring the rate of conversion of GTP to GDP by the α subunit in the presence of the agent compared to the rate in the absence of the agent. An increase in the rate of conversion indicates that the agent is a taste stimulator and a decrease in the rate of conversion indicates that the agent is a taste inhibitor.

A second type of method identifies taste modifying agents that mimic or block the effect of gustducin γ subunit on an effector. The method includes the steps of incubating gustducin γ subunit associated in biologically active form with a G protein β subunit (e.g., Gβ1 or Gβ2) and phospholipase C, adding $^3$H-myoinositol in the presence and absence of an agent, and measuring inositol trisphosphate generation in the presence of the agent in comparison to in the absence of the agent. An increase in inositol trisphosphate generation indicates the agent is a taste stimulator and a decrease in inositol trisphosphate generation indicates that the agent is a taste inhibitor.

Peptides (e.g., fragments of antibodies to gustducin γ subunit and peptides corresponding to portions of gustducin γ subunit) that mimic or compete with a binding activity of the gustducin γ subunits may be taste modifying agents. These peptides are likely to affect the interaction of the gustducin/transducin γ subunits with sensory receptors, cellular effectors and/or their associated α and β subunits. Examples of taste modifying peptides contemplated by the invention are: a) peptides comprising about amino acid 1 through about amino acid 14 of SEQ ID NO: 7, b) peptides comprising about amino acid 18 through about amino acid 32 of SEQ ID NO: 7, c) peptides comprising about amino acid 31 through about amino acid 40 of SEQ ID NO: 7, d) peptides comprising about amino acid 47 through amino acid 59 of SEQ ID NO: 7, and e) peptides comprising about amino acid 56 through about amino acid 67 of SEQ ID NO: 7. Peptides of a) correspond to regions involved in the interaction of gustducin γ subunit with the a subunit and effectors such as PLC. Peptides of c) correspond to regions involved in the interaction of the gustducin γ subunit with β subunit. Peptides of e) correspond to regions involved in the interaction of the gustducin γ subunit with taste receptor. Antibodies specific for peptides of b) and d) blocked the generation of IP$_3$ in taste tissue. Lipid modification (e.g., farnesylated or geranylgeranylated) of the carboxy terminus of peptides of c) is expected to enhance the taste modifying activity of the peptides.

While the present invention has been described in terms of preferred embodiments, it is understood that variations and improvements will occur to those skilled in the art. Therefore, it is intended that the appended claims cover all such equivalent variations which come within the scope of the invention as claimed.

The invention claimed is:

1. A method for identifying an agent which stimulates or inhibits taste comprising the steps of a) incubating gustducin γ with a G protein β subunit and phospholipase C, wherein the gustducin γ is selected from the group of (i) a polypeptide having an amino acid sequence of SEQ ID NO: 2, SEQ ID NO: 4, SEQ ID NO: 7, or SEQ ID NO: 9, (ii) a polypeptide encoded by the polynucleotide of SEQ ID NO: 1, SEQ ID NO: 3, SEQ ID NO: 5, SEQ ID NO: 6, or SEQ ID NO: 8, and (iii) a polypeptide that is capable of activating phospholipase C in the presence of an agent which stimulates or inhibits taste and a G protein β subunit and that has at least 90% identity to the polypeptide of SEQ ID NO: 7; b) adding an agent; and c) measuring inositol triphosphate generation in the presence of the agent in comparison to in the absence of the agent, wherein an increase in inositol triphosphate generation in the presence of the agent indicates the agent is a taste stimulator and a decrease in inositol triphosphate generation in the presence of the agent indicates that the agent is a taste inhibitor.

2. The method according to claim 1, wherein the G protein β subunit is Gβ1 or G62 2.

3. The method according to claim 2, wherein the G protein β subunit is Gβ1.

4. The method according to claim 2, wherein the G protein β subunit is Gβ2.

5. The method according to claim 1, wherein the phospholipase C is phospholipase Cβ2.

6. The method according to claim 1 further comprising: adding $^3$H-myoinositol after said incubating and prior to said measuring.

7. The method according to claim 1, wherein the gustducin γ is a polypeptide having an amino acid sequence of SEQ ID NO: 2, SEQ ID NO: 4, SEQ ID NO: 7, or SEQ ID NO: 9.

8. The method according to claim 1, wherein the gustducin γ is a polypeptide encoded by the polynucleotide of SEQ ID NO: 1, SEQ ID NO: 3, SEQ ID NO: 5, SEQ ID NO: 6, or SEQ ID NO: 8.

9. The method according to claim 1, wherein the gustducin γ is a polypeptide that is capable of activating phospholipase C in the presence of an agent which stimulates or inhibits taste and a G protein β subunit and that has at least 90% identity to the polypeptide of SEQ ID NO: 7.

10. The method according to claim 9, wherein the gustducin γ is a polypeptide that has at least 95% identity to the polypeptide of SEQ ID NO: 7.

* * * * *

UNITED STATES PATENT AND TRADEMARK OFFICE
CERTIFICATE OF CORRECTION

PATENT NO. : 7,314,716 B2 Page 1 of 1
APPLICATION NO. : 10/161941
DATED : January 1, 2008
INVENTOR(S) : Huang et al.

It is certified that error appears in the above-identified patent and that said Letters Patent is hereby corrected as shown below:

Col. 1 at line 7, insert --This invention was made with government support under grant numbers DC003155, MH057241, and DC000310 awarded by the National Institutes of Health. The government has certain rights in this invention.--.

Signed and Sealed this

Sixteenth Day of March, 2010

David J. Kappos
*Director of the United States Patent and Trademark Office*